United States Patent
Aoki

(10) Patent No.: US 10,829,482 B2
(45) Date of Patent: Nov. 10, 2020

(54) METHOD FOR PRODUCING GLYCERIC ACID ESTER

(71) Applicant: KAO CORPORATION, Tokyo (JP)

(72) Inventor: Takashi Aoki, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/473,177

(22) PCT Filed: Dec. 26, 2017

(86) PCT No.: PCT/JP2017/046815
§ 371 (c)(1),
(2) Date: Jun. 24, 2019

(87) PCT Pub. No.: WO2018/124149
PCT Pub. Date: Jul. 5, 2018

(65) Prior Publication Data
US 2019/0322654 A1    Oct. 24, 2019

(30) Foreign Application Priority Data

Dec. 27, 2016  (JP) ................ 2016-253829
Dec. 27, 2016  (JP) ................ 2016-253833
Dec. 27, 2016  (JP) ................ 2016-253836
Dec. 27, 2016  (JP) ................ 2016-253843

(51) Int. Cl.
| | |
|---|---|
| C07D 319/06 | (2006.01) |
| C07D 317/32 | (2006.01) |
| C07C 215/10 | (2006.01) |
| C07C 45/65 | (2006.01) |
| C07C 49/17 | (2006.01) |
| C07D 407/12 | (2006.01) |
| C07B 61/00 | (2006.01) |
| C07C 213/00 | (2006.01) |
| C07B 41/12 | (2006.01) |

(52) U.S. Cl.
CPC ............ C07D 407/12 (2013.01); C07B 61/00 (2013.01); C07C 45/65 (2013.01); C07C 213/00 (2013.01); C07D 317/32 (2013.01); C07D 319/06 (2013.01); C07B 41/12 (2013.01); C07C 49/17 (2013.01); C07C 215/10 (2013.01)

(58) Field of Classification Search
CPC ....... C07D 317/32; C07C 45/65; C07C 49/17; C07C 215/10; C07C 319/06; C07C 213/00
USPC .......................................................... 549/430
See application file for complete search history.

(56) References Cited

U.S. PATENT DOCUMENTS

| | | |
|---|---|---|
| 5,821,374 A | 10/1998 | Jenny et al. |
| 7,851,639 B2 | 12/2010 | Hayat et al. |
| 2007/0197790 A1 | 8/2007 | Belgsir et al. |
| 2012/0014889 A1 | 1/2012 | Miller et al. |

FOREIGN PATENT DOCUMENTS

| | | |
|---|---|---|
| CN | 1939904 A | 4/2007 |
| CN | 101412706 A | 4/2009 |
| DE | 3900479 A1 | 7/1990 |
| EP | 1669353 A1 | 6/2006 |
| JP | 2006-219406 A | 8/2006 |

(Continued)

OTHER PUBLICATIONS

Waidmann et al. Energy Enveron. Sci, 5, 7771-7780, ,2012.*

(Continued)

*Primary Examiner* — Venkataraman Balasubramanian
(74) *Attorney, Agent, or Firm* — Birch, Stewart, Kolasch & Birch, LLP

(57) ABSTRACT

The present invention is to provide a method of producing a glyceric acid ester which is easy for production and high in yield, and in which a pyridine to be used for the reaction is easily reused. Provided is a method of producing a compound represented by the following formula (II), including a step of oxidatively esterifying Compound A represented by the following formula (I) with Compound B selected from an organic nitroxyl radical, an N-hydroxy form thereof, and a salt containing an oxo ammonium cation of them, and an oxidizing agent in the presence of a pyridine having an alkyl substituent, wherein the use amount of Compound B is 0.0001 or more and 0.1 or less in terms of a molar ratio relative to Compound A:

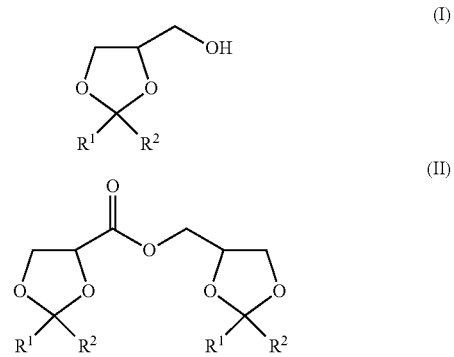

wherein, in the formulae (I) and (II), $R^1$ and $R^2$ each independently represent a hydrogen atom or a monovalent hydrocarbon group, or $R^1$ and $R^2$ are bonded to each other to form a divalent hydrocarbon group for constituting a ring structure.

11 Claims, 1 Drawing Sheet

(56) References Cited

FOREIGN PATENT DOCUMENTS

| WO | WO 2012/041845 A1 | 4/2012 |
|---|---|---|
| WO | WO 2014/140017 A1 | 9/2014 |
| WO | WO 2015/181747 A1 | 12/2015 |
| WO | WO 2016/097840 A1 | 6/2016 |

OTHER PUBLICATIONS

Abramovich et al., "Organocatalytic Oxidative Dimerization of Alchols to Esters", Synlett, vol. 23, No. 15, pp. 2261-2265.
Badalyan et al., "Cooperative Electrocatalytic Alcohol Oxidation with Electron-Proton Transfer Mediators", Nature, vol. 535, No. 7612, 2016, pp. 406-410.
De Luca et al., "Trichloroisocyanuric/TEMPO Oxidation of Alcohols under Mild Conditions: A Close Investigation", Journal of Organic Chemistry, vol. 68, No. 12, 2003, pp. 4999-5001.
English translation of Decision to Grant a Patent for Japanese Patent Application No. 2017-250263, dated Aug. 24, 2018.
English translation of Decision to Grant a Patent for Japanese Patent Application No. 2017-250264, dated Aug. 15, 2018.
English translation of Decision to Grant a Patent for Japanese Patent Application No. 2017-250267, dated Aug. 24, 2018.
English translation of Decision to Grant a Patent for Japanese Application No. 2017-250262, dated Aug. 28, 2018.
English translatin of Notice of Reasons for Refusal for Japanese Patent Application No. 2017-250262, dated Jun. 18, 2018.
English translation of Notice of Reasons for Refusal for Japanese Patent Application No. 2017-250263, dated Jun. 4, 2018.
English translation of Notice of Reasons for Refusal for Japanese Patent Application No. 2017-250264, dated Jun. 4, 2018.
English translation of Notice of Reasons for Refusal for Japanese Patent Application No. 2017-250267, dated Jun. 4, 2018.
Ermolenko et al., "An Expedient One-Step Preparation of (S)-2,3,-O-Isopropylidene-glyceraldehyde", Synlett, vol. 10, 2001, pp. 1565-1566.
Hamlin et al., "Dehydrogenation of Prfluoroalkyl Ketones by Using a Recyclable Oxoammonium Salt", European Journal of Organic Chemistry, vol. 18, 2013, pp. 3658-3661.
Herath et al. 2,2,6,6-Tetramethyl piperidine-1-oxyl (TEMPO)-mediated catalytic oxidation of benzyl alcolhol in acetonitrile and ionic liquid 1-butyl-3-methyl-imidazolium hexafluorophosphate [BMim][PF$_6$]: Kinetic analysis, Electrochimica Acta, vol. 53, No. 12, 2008, pp. 4324-4330.
Hon et al., "Tishchenko Reactions and Oppenauer Oxidation Reactions of Aldehydes Promoted by Diisobutylaluminum Hydride", Tetrahedron Letters, vol. 45, No. 16, 2004, pp. 3313-3315.
Hon et al., "Tischenko Reactions of Aldehydes Promoted by Diisobutylaluminum Hydride and its Application of the Macrocyclic Lactone Formation", Tetrahedron, vol. 63, No. 46, 2007, pp. 11325-11340.
International Search Report for International Application No. PCT/JP2017/046815 dated Feb. 6, 2018.
Kataky et al., "Chiral Resolution of R and S 1-Phenylethanol on Glassy Carbon Electrodes", Journal of Electroanalytical Chemistry, vol. 633, No. 1, 2009, pp. 57-62.
Li et al., "α-Aminoxylation of Ketones and β-Chloro-α-aminoxylation of Enones with TEMPO and Chlorocatecholborane", Organic Letters, vol. 14, No. 17, 2012, pp. 4474-4477.
Merbouh et al., "Oxoammonium Salts. 9. Oxidative Dimerization of Polyfunctional Primary Alcohols to Esters. An Interesting β Oxygen Effect", Journal of Organic Chemistry, vol. 69, No. 15, 2004, pp. 5116-5119.
Shibuya et al., "2-Azaadamantane N-Oxyl (AZADO and I-Me-AZADO: High Efficient Organocatalysts for Oxidation of Alcohols", Journal of the American Chemical Society, vol. 128, No. 26, 2006, pp. 8412-8413.
Sorbye et al., Preparation of Protected Serinol, Synthetic Communications, vol. 27, No. 16, 1997, pp. 2813-2816.
Wang et al., "Domino Radical Addition/Oxidation Sequence with Photocatalysis: One-Pot Synthesis of Polysubstituted Furans from α-Chloro-Alkyl Ketones and Styrenes", Chemistry A European Journal, vol. 22, No. 39, Aug. 19, 2016, pp. 13794-13798.
Wang et al., "The indirect conversion of glycerol into 1,3-dihydroxyacetone over magnetic polystyrene immobilized TEMPO catalyst", Chemical Engineering Journal, vol. 229, 2013, pp. 234-238.
Zheng et al. "Novel Process for 1,3-Dihydroxyacetone Production from Glycerol. 1. Technological Feasibility Study and Process Design" Industrial & Engineering Chemistry Research, vol. 51, 2012, pp. 3715-3721.
U.S. Appl. No. 16/473,065, filed Jun. 24, 2019.
U.S. Appl. No. 16/473,167, filed Jun. 24, 2019.
Bobbitt et al., "Oxoammonium Salt Oxidations of Alcohols in the Presence of Pyridine Bases," J. Org.Chem., vol. 79, No. 3, 2014 (Date of Publication Jan. 6, 2014), pp. S1-S56 (57 total pages).
Cao et al., "Aerobic Oxidation Catalysis with Stable Radicals," Chem. Commun, vol. 50, 2014 (Published on Mar. 12, 2014), pp. 4524-4543.
Indian Office Action, dated Oct. 1, 2019, for Indian Application No. 201917000304, with an English translation.
Indian Office Action, dated Oct. 11, 2019, for Indian Application No. 201917000294, with an English translation.
Indian Office Action, dated Oct. 4, 2019, for Indian Application No. 201917000301, with an English translation.
Okada et al., "Sodium Hypochlorite Pentahydrate (NaOCl·5H$_2$0) Crystals as an Extraordinary Oxidant for Primary and Secondary Alcohols," Synlett, vol. 25, No. 4, 2014, pp. 596-598 (5 total pages).
Animati et al., "Synthesis and Biological Evaluation of Rebeccamycin Analogues Modified at the Imide Moiety, " Bioorganic & Medicinal Chemistry Letters, vol. 22, 2012 (Available online Jun. 15, 2012), pp. 5013-5017.
Carlsen et al., "Synthesis of Benzylidene-Protected Dihydroxyacteone, " Acta Chemica Scandinavica, vol. 50, 1996, pp. 185-187.
European Patent Office Communication and extended search report issued in the corresponding European Patent Application No. 17888167.8 dated Jul. 14, 2020.
Majewski et al., "1.3-Dioxan-5-one: synthesis, deprotonation, and reactions of their lithium enolates, " Canadian Journal of Chemistry, vol. 73, No. 10, 1995, pp. 1616-1626.
International Search Report for International Application No. PCT/JP2017/046813 dated Mar. 20, 2018.
International Search Report for International Application No. PCT/JP2017/046814 dated Feb. 6, 2018.
Trost et al., "Palladium-Catalyzed Trimethylenemethane Reaction To Form Methylenetetrahydrofurans. Aldehyde and Ketone Substrates and the Tin Effect," Journal of the American Chemical Society, vol. 111, No. 15, 1989, pp. 5902-5915.
Extended European Search Report dated Aug. 17, 2020 for Application No. 17885459.2.
Sproge et al., "Selective liquid phase oxidation of glycerol to glyceric acid over novel supported Pt catalysts", J. Serb. Chem. Soc, vol. 78, No. 9, 2013, pp. 1359-1372.

* cited by examiner

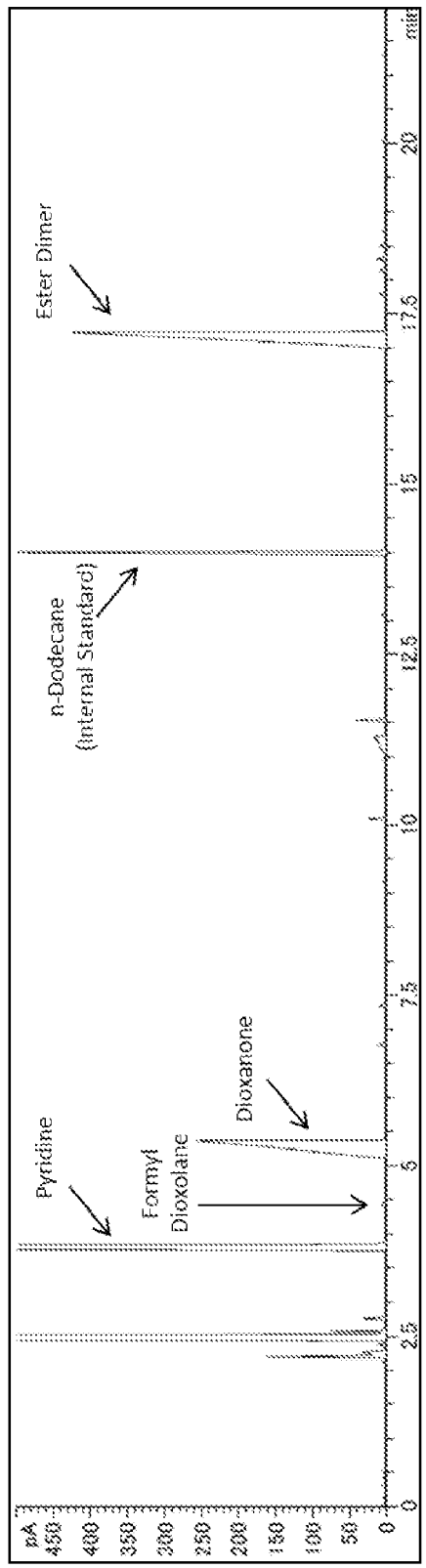

METHOD FOR PRODUCING GLYCERIC ACID ESTER

FIELD OF THE INVENTION

The present invention relates to a method of producing a glyceric acid ester.

BACKGROUND OF THE INVENTION

Compounds having a glyceric acid skeleton in which hydroxy groups at the 2-position and 3-position are protected as a cyclic acetal group are useful as a synthetic intermediate for glyceric acid and an ester thereof having applications as raw materials, for example, for various medicaments, cosmetics, detergents, polymers, or the like.

As for examples of the compounds having a glyceric acid skeleton in which hydroxy groups at the 2-position and 3-position are protected as a cyclic acetal group, for example, Synlett, Vol. 23, pp. 2261-2265, 2012 (NPL 1) describes a production example of (2,2-dimethyl-1,3-dioxolan-4-yl)methyl 2,2-dimethyl-1,3-dioxolane-4-carboxylate through oxidative dimerization (oxidative esterification) of 4-hydroxymethyl-2,2-dimethyl-1,3-dioxolane with 2,2,6,6-tetramethylpiperidine-1-oxyl (hereinafter also referred to as "TEMPO"), an oxidizing agent, and pyridine.

SUMMARY OF THE INVENTION

The present invention relates to a method of producing a compound represented by the following formula (II), including a step of oxidatively esterifying Compound A represented by the following formula (I) with Compound B selected from an organic nitroxyl radical, an N-hydroxy form thereof, and a salt containing an oxo ammonium cation of them, and an oxidizing agent in the presence of a pyridine having an alkyl substituent, wherein the use amount of Compound B is 0.0001 or more and 0.1 or less in terms of a molar ratio relative to Compound A:

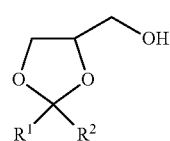

(I)

wherein, in the formula (I), $R^1$ and $R^2$ each independently represent a hydrogen atom or a monovalent hydrocarbon group, or $R^1$ and $R^2$ are bonded to each other to form a divalent hydrocarbon group for constituting a ring structure; and

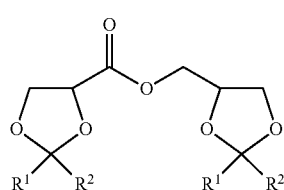

(II)

wherein, in the formula (II), $R^1$ and $R^2$ each independently represent a hydrogen atom or a monovalent hydrocarbon group, or $R^1$ and $R^2$ are bonded to each other to form a divalent hydrocarbon group for constituting a ring structure.

BRIEF DESCRIPTION OF THE DRAWING

FIG. 1 is a GC chart of a reaction solution obtained in Comparative Example 1-1.

DETAILED DESCRIPTION OF THE INVENTION

[Production Method of Compound Represented by Formula (II)]

The method of producing a compound represented by the following formula (II) (hereinafter also referred to as "glyceric acid ester" or "ester dimer") of the present invention includes a step of oxidatively esterifying Compound A represented by the following formula (I) (hereinafter also referred to as "dioxolane") with Compound B selected from an organic nitroxyl radical, an N-hydroxy form thereof, and a salt containing an oxo ammonium cation of them, and an oxidizing agent in the presence of a pyridine having an alkyl substituent (this step will be hereinafter also referred to as "step 2"). In the step 2, the use amount of Compound B is 0.0001 or more and 0.1 or less in terms of a molar ratio relative to Compound A.

In the following description, the compound represented by the formula (II) which is obtained by the production method of the present invention is also referred to as "glyceric acid ester of the present invention" or "ester dimer of the present invention".

NPL 1 explicitly expresses the broadness of an application range of the raw material alcohol of this reaction according to the reaction results using a large number of alcohols. Meanwhile, from the viewpoint of oxidative esterification yield, there is a description that only pyridine is usable as a base that is essential for the reaction. In order to industrialize this reaction method using a large excess amount of pyridine relative to the raw material alcohol, it is very important from the viewpoint of economy that pyridine is regenerated and reused from a pyridine salt to be by produced in a large amount after the reaction.

As for the regeneration method of pyridine, it may be considered that a method of adding a strong base aqueous solution, such as sodium hydroxide, in an equivalent amount or more amount to the pyridine salt, thereby liberating the pyridine is the most general. However, since the pyridine is mingled with water, it is difficult to recover the regenerated pyridine in a high yield through extraction with an organic solvent. In addition, though it is possible to distil and recover the pyridine in an aqueous phase, since the pyridine has physical properties such that it is azeotropic with water, in order to obtain pyridine that is anhydrous or has a water content close to the anhydrous state, an aspect of which is necessary for the reuse, a special dehydration treatment becomes necessary, and such is disadvantageous from the viewpoint of economy.

The present invention relates to providing a production method of a glyceric acid ester which is easy for production and high in yield, and in which a pyridine to be used for the reaction is easily reused.

In accordance with the present invention, a method of producing a glyceric acid ester which is easy for production and high in yield, and in which a pyridine to be used for the reaction is easily reused, can be provided. Furthermore, glyceric acid and an esterified product thereof can be produced from the ester dimer obtained according to the present invention, and a compound represented by the following formula (II) is also useful as intermediates for various useful substances.

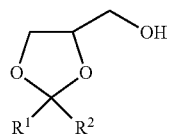

(I)

In the formula (I), $R^1$ and $R^2$ each independently represent a hydrogen atom or a monovalent hydrocarbon group, or $R^1$ and $R^2$ are bonded to each other to form a divalent hydrocarbon group for constituting a ring structure.

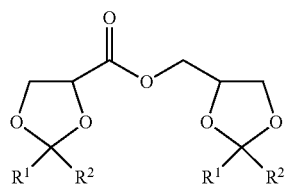

(II)

In the formula (II), $R^1$ and $R^2$ each independently represent a hydrogen atom or a monovalent hydrocarbon group, or $R^1$ and $R^2$ are bonded to each other to form a divalent hydrocarbon group for constituting a ring structure.

In the formulae (I) and (II), $R^1$ and $R^2$ each independently represent a hydrogen atom or a monovalent hydrocarbon group, or $R^1$ and $R^2$ are bonded to each other to form a divalent hydrocarbon group for constituting a ring structure.

As a preferred embodiment of $R^1$ and $R^2$, $R^1$ is a hydrogen atom, and $R^2$ is a hydrogen atom or a monovalent hydrocarbon group. The carbon number of the monovalent hydrocarbon group is preferably 1 or more and 20 or less. The hydrocarbon group for $R^2$ is preferably an alkyl group or an aryl group. The carbon number of the alkyl group is preferably 1 or more, and it is preferably 20 or less, more preferably 18 or less, still more preferably 16 or less, yet still more preferably 14 or less, yet still more preferably 12 or less, yet still more preferably 10 or less, yet still more preferably 8 or less, yet still more preferably 6 or less, yet still more preferably 4 or less, and yet still more preferably 2 or less. Such an alkyl group may be either linear or branched. In addition, the carbon number of the aryl group for $R^2$ is preferably 6 or more, and it is preferably 20 or less, more preferably 18 or less, still more preferably 16 or less, yet still more preferably 14 or less, yet still more preferably 12 or less, yet still more preferably 10 or less, yet still more preferably 8 or less, and yet still more preferably 6 or less. From the aforementioned viewpoint, $R^2$ is preferably a hydrogen atom or a monovalent hydrocarbon group having 1 or more and 20 or less carbon atoms, more preferably a hydrogen atom or a linear alkyl group having 1 or more and 8 or less carbon atoms, a branched alkyl group having 1 or more and 8 or less carbon atoms, or an aryl group having 6 or more and 20 or less carbon atoms, still more preferably a hydrogen atom, a methyl group, or a phenyl group, and yet still more preferably a hydrogen atom.

As another preferred embodiment of $R^1$ and $R^2$, from the viewpoints of availability of raw material and reactivity, stability of the dioxolane and the ester dimer of the present invention, and easiness of recovery of a ketone by-produced through acetal decomposition of the ester dimer of the present invention, $R^1$ and $R^2$ are each a monovalent hydrocarbon group. Preferably, $R^1$ is a monovalent hydrocarbon group having 1 or more and 8 or less carbon atoms, and $R^2$ is a monovalent hydrocarbon group having 2 or more and 8 or less carbon atoms; more preferably, $R^1$ is an alkyl group having 1 or more and 8 or less carbon atoms, and $R^2$ is an alkyl group having 2 or more and 8 or less carbon atoms; still more preferably, $R^1$ is an alkyl group having 1 or 2 carbon atoms, and $R^2$ is an alkyl group having 2 or more and 6 or less carbon atoms; yet still more preferably, $R^1$ is an alkyl group having 1 or 2 carbon atoms, and $R^2$ is an alkyl group having 2 or more and 4 or less carbon atoms; yet still more preferably, $R^1$ is a methyl group, and $R^2$ is an ethyl group.

As another preferred embodiment of $R^1$ and $R^2$, $R^1$ and $R^2$ are bonded to each other to form a divalent hydrocarbon group for constituting a ring structure, and from the aforementioned viewpoints, $R^1$ and $R^2$ are preferably bonded to each other to form a divalent hydrocarbon group having 2 or more and 7 or less carbon atoms, more preferably a divalent hydrocarbon group having 3 or more and 6 or less carbon atoms, still more preferably a divalent hydrocarbon group having 4 or more and 5 or less carbon atoms, yet still more preferably a divalent hydrocarbon group having 5 carbon atoms. That is, the ring structure containing $R^1$ and $R^2$ is preferably a 3- to 8-membered ring, more preferably a 4- to 7-membered ring, still more preferably a 5- to 6-membered ring, and yet still more preferably a 6-membered ring. The ring structure containing $R^1$ and $R^2$ is preferably a cycloalkane structure, more preferably a ring structure having 5 or 6 carbon atoms (cyclopentane ring or cyclohexane ring), and still more preferably a cyclohexane ring.

In the formula (I), in the case where $R^1$ and $R^2$ are bonded to each other to constitute a ring structure, the formula (I) becomes the following formula (I'); and similarly, in the formula (II), in the case where $R^1$ and $R^2$ are bonded to each other to constitute a ring structure, the formula (II) becomes the following formula (II').

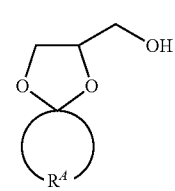

(I')

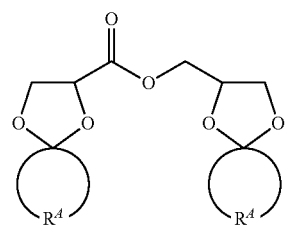

(II')

In the formulae (I') and (II'), $R^4$'s each indicate a divalent hydrocarbon group to form a ring structure.

In the formulae (I') and (II'), the ring structure containing $R^4$ is preferably a 3- to 8-membered ring, more preferably a 4- to 7-membered ring, still more preferably a 5- to 6-membered ring, and yet still more preferably a 6-membered ring. The ring structure containing $R^4$ is preferably a cycloalkane structure, and as mentioned above, it is preferred that a cyclopentane ring or a cyclohexane ring is formed, and it is more preferred that a cyclohexane ring is formed.

That is, $R^4$ is preferably an ethylene group (—$(CH_2)_2$—), a trimethylene group (—$(CH_2)_3$—), a tetramethylene group ((—$(CH_2)_4$—), a pentamethylene group (—$(CH_2)_5$—), a hexamethylene group (—$(CH_2)_6$—), or a heptamethylene group (—$(CH_2)_7$—), more preferably a trimethylene group, a tetramethylene group, a pentamethylene group, or a hexamethylene group, still more preferably a tetramethylene group or a pentamethylene group, and yet still more preferably a pentamethylene group.

In the compound represented by the formula (I), one or more asymmetric carbons are existent. In consequence, the compound represented by the formula (I) is existent as a racemate or a stereoisomer mixture unless an enantioselective reaction or separation of stereoisomers is applied.

In the present invention, a stereoisomer ratio of the compound represented by the formula (I) is not particularly limited.

In the dioxolane of the formula (I), since one or more asymmetric carbons are existent, the ester dimer of the formula (II) is obtained as a stereoisomer mixture unless a dioxolane having an enantiomeric excess of 100% is used.

In the present invention as for the compound represented by the formula (I), a marketed product may be used, the compound may be produced and used, and there is no particular limitation. However, in the present invention, from the viewpoint of inexpensive production, it is preferred that the dioxolane is produced by the following method.

<Step 1: Production Method of Dioxolane>

It is preferred that the production method of a compound represented by the formula (II) according to the present invention includes a step of producing a compound (dioxolane) represented by the formula (I) (hereinafter also referred to as "step 1") prior to the step 2.

The method of producing the dioxolane (the compound represented by the formula (I)), which is used in the present invention, is not limited, and from the viewpoints of availability of raw material, yield, and easiness of reaction operation, the compound is preferably produced by a method of acetalizing glycerol, and a compound represented by the following formula (III) in the presence of an acid catalyst (method 1), or a method of subjecting glycerol and a compound represented by the following formula (IV) to acetal exchange in the presence of an acid catalyst (method 2), both of which are generally widely known.

That is, it is preferred that the production method of a glyceric acid ester of the present invention includes the following step 1 and step 2.

Step 1: A step of acetalizing glycerol and a compound represented by the following formula (III) or a multimer thereof in the presence of an acid catalyst (step 1-1), or a step of subjecting glycerol and a compound represented by the following formula (IV) to acetal exchange in the presence of an acid catalyst (step 1-2)

Step 2: A step of oxidatively esterifying a mixture of a compound represented by the following formula (I) and a compound represented by the following formula (V)

(III)

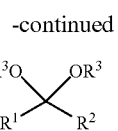

(IV)

In the formulae (III) and (IV), $R^1$ and $R^2$ are synonymous with $R^1$ and $R^2$ in the formula (II), and $R^3$'s each independently represent a monovalent hydrocarbon group.

In the formula (IV), $R^3$'s each independently represent a monovalent hydrocarbon group, from the viewpoint of availability of raw material, $R^3$ is preferably a hydrocarbon group having 1 or more and 8 or less carbon atoms, and from the viewpoint of promoting a reaction by distilling an alcohol by-produced by the acetal exchange reaction outside the reaction system, $R^3$ is more preferably a monovalent hydrocarbon group having 1 or more and 3 or less carbon atoms, still more preferably a monovalent alkyl group having 1 or more and 3 or less carbon atoms, and yet still more preferably a methyl group.

The method 1 and method 2 (step 1-1 and step 1-2) are shown below.

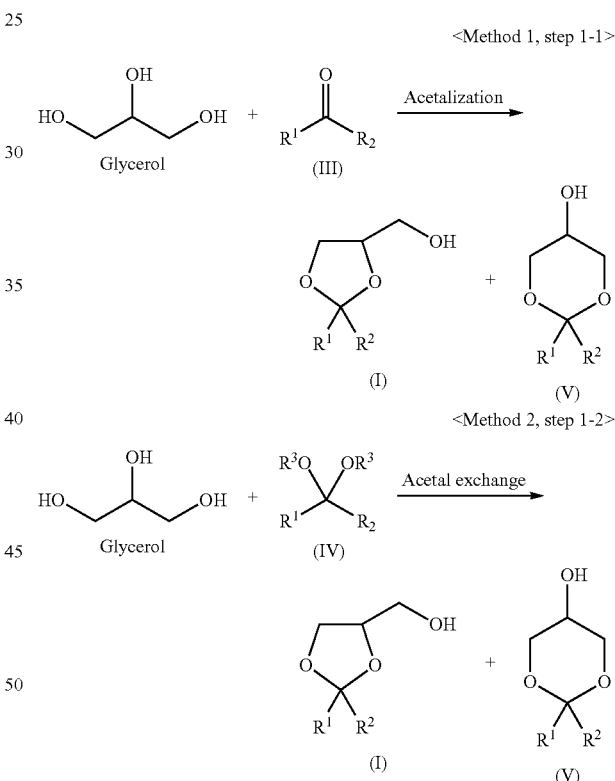

The dioxolane obtained by the aforementioned acetalization or acetal exchange method is obtained as an isomer mixture containing the compound represented by the formula (V) (hereinafter also referred to as "dioxane") as expressed by the aforementioned reaction formula. Though an isomer ratio of the dioxolane and the dioxane is not limited, from the viewpoints of productivity and economy, it is preferred that the isomerization ratio of the dioxolane is high as far as possible.

The isomerization ratio of the dioxolane obtained by a general production method from a compound represented by the formula (III) or (IV) wherein at least one of $R^1$ and $R^2$ is a hydrogen atom (hereinafter also referred to as "aldehyde") is 40% or more and 60% or less. In addition, the isomerization ratio of the dioxolane obtained the aforementioned general production method from a compound represented by the formula (III) or (IV) wherein all of $R^1$ and $R^2$ are not a hydrogen atom (hereinafter also referred to as "ketone") is 95% or more. In consequence, the ketone is preferred from the viewpoint that the isomerization ratio of the dioxolane is high.

Meanwhile, in the case of oxidatively esterifying the dioxolane obtained from the aldehyde, the yield of the ester dimer of the present invention tends to be predominantly high as compared with the case of using the ketone as the raw material. The aldehyde is preferred from the viewpoints that the reaction readily proceeds and that it has such an aspect that the acetal group is stable, and also the viewpoint that the ester dimer of the present invention is obtained in a high yield.

The mixture of the dioxolane (compound represented by the formula (I)) and the dioxane (compound represented by the formula (V)) obtained in the aforementioned method 1 or method 2 can be used as it is, or after being purified, as the raw material in the subsequent step, and from the viewpoint of the yield in the subsequent step, it is preferred that the mixture is purified to remove an unreacted raw material, etc., and from the viewpoint of easiness of purification, it is more preferred to perform distillation purification.

In view of the matter that it is difficult to separate the dioxolane and the dioxane from each other through purification, it is preferred to use the dioxolane and the dioxane in a state of mixture as the raw material for the subsequent step.

<Step 2: Oxidative Esterification>

The glyceric acid ester of the present invention (compound represented by the formula (II)) is obtained through oxidative esterification of the aforementioned dioxolane (compound represented by the formula (I)).

The oxidative esterification is one kind of oxidation reaction for obtaining an ester from a primary alcohol and an alcohol in a broad sense and is more generally a reaction for obtaining one molecule of an ester dimer from two molecules of the same primary alcohol, and also has another name, such as oxidative dimerization. In the present invention, the oxidative esterification means that a reaction of obtaining the ester dimer of the present invention (compound represented by the formula (II)) from the dioxolane (compound represented by the formula (I)) is performed.

When the mixture of the dioxolane (compound represented by the formula (I)) and the dioxane (compound represented by the formula (V)) is oxidatively esterified, the following reaction occurs representatively.

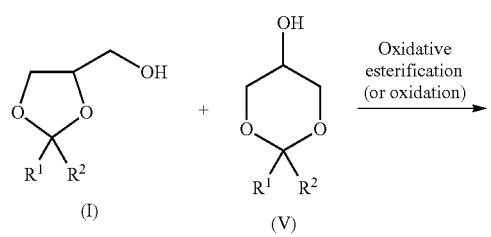

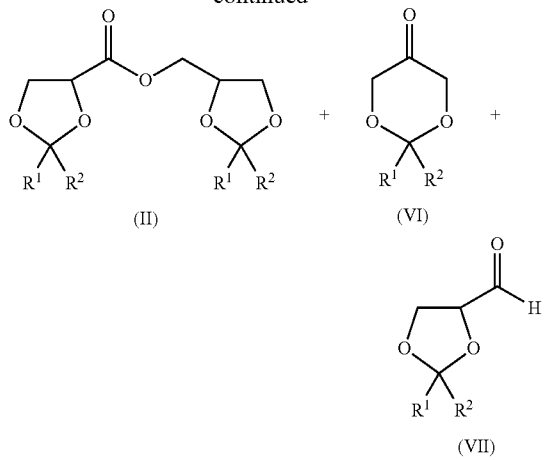

In the formula, $R^1$ and $R^2$ are the same as mentioned above.

The present invention has a feature that the oxidative esterification is performed in the presence of a pyridine having an alkyl substituent. The step 2 is an oxidative esterification method of using at least one selected from an organic nitroxyl radical, an N-hydroxy form thereof, and a salt containing an oxo ammonium cation of them (hereinafter also referred to as "nitroxyl radical species"), an oxidizing agent, and a pyridine having an alkyl substituent.

As mentioned above, the dioxolane to be used in the present invention is typically a mixture containing the dioxane, and in the oxidative esterification step, a formyl dioxolane (compound represented by the formula (VII)) may be occasionally by-produced depending upon the reaction conditions. The by-production quantity of the formyl dioxolane is not limited, and from the viewpoint of obtaining the ester dimer of the present invention in a high yield, the yield of the formyl dioxolane produced from the dioxolane is preferably 20% or less, more preferably 10% or less, still more preferably 5% or less, yet still more preferably substantially 0%, and even yet still more preferably 0%. In order to decrease the by-production quantity of the formyl dioxolane, a preferred production method as mentioned later may be adopted.

Similarly, in the step of oxidatively esterifying the mixture of the dioxolane and the dioxane, there is a possibility depending upon the reaction conditions that the dioxane does not react, a compound represented by the formula (VI) (hereinafter also referred to as "dioxanone") is produced from the dioxane, or a compound other than the dioxanone is produced, or a mixture of these compounds is obtained. However, so far as the purification step of the ester dimer of the present invention is not adversely affected, the production quantity or production ratio of these compounds is not limited.

[Pyridine Having Alkyl Substituent]

In the present reaction, for the purpose of neutralizing an acid by-produced due to consumption of the oxidizing agent, or the like, a pyridine having an alkyl substituent is used. The pyridine having an alkyl substituent may have at least one alkyl substituent, and the number of alkyl substituent is 1 to 5, preferably 1 to 4, more preferably 1 to 3, and still more preferably 1 or 2. The alkyl substituents each independently have a carbon number of preferably 1 or more, and preferably 12 or less, more preferably 10 or less, still more preferably 8 or less, yet still more preferably 6 or less, yet still more preferably 4 or less, and yet still more preferably 2 or less. Though the alkyl group may be linear, a branched form, or cyclic, it is preferably linear or branched, and more preferably linear.

Preferred examples of the pyridine having an alkyl substituent include 2-methylpyridine, 3-methylpyridine, 4-methylpyridine, 2-ethylpyridine, 3-ethylpyridine, 4-ethylpyridine, 2-propylpyridine, 3-propylpyridine, 4-propylpyridine, 3-n-butylpyridine, 4-tert-butylpyridine, 2-amylpyridine, 4-amylpyridine, 2-(3-pentyl)pyridine, 4-(3-penyl)pyridine, 2,3-lutidine (another name: 2,3-dimethylpyridine), 2,4-lutidine (another name: 2,4-dimethylpyridine), 2,5-lutidine (another name: 2,5-dimethylpyridine), 2,6-lutidine (another name: 2,6-dimethylpyridine), 3,4-lutidine (another name: 3,4-dimethylpyridine), 3,5-lutidine (another name: 3,5-dimethylpyridine), 5-ethyl-2-methylpyridine, 2,6-di-tert-butylpyridine, 2,3,5-collidine (another name: 2,3,5-trimethylpyridine), and 2,4,6-collidine (another name: 2,4,6-trimethylpyridine).

From the viewpoints of availability and water insolubility, the pyridine having an alkyl substituent is preferably a pyridine having an alkyl substituent at at least one position selected from the 3-position, the 4-position, and the 5-position. In addition, from the viewpoint of obtaining the ester dimer of the present invention in a higher yield, the pyridine is preferably a pyridine not having an alkyl substituent at the 2-position and the 6-position. That is, a pyridine having an alkyl substituent only at one or more and three or less positions selected from the 3-position, the 4-position, and the 5-position among the 1- to 6-positions of the pyridine is preferred. From the viewpoints of having an appropriate boiling point and an equipment load at the time of distillation purification, a pyridine whose alkyl substituent each independently has 1 or more and 4 or less carbon atoms is more preferred.

From the viewpoints of availability and water insolubility and the viewpoint of easiness of recovery, as the pyridine having an alkyl substituent, at least one selected from 5-ethyl-2-methylpyridine, 3,5-lutidine, 2,6-lutidine, 2,6-tert-butylpyridine, 3-ethylpyridine, 4-methylpyridine, and 4-ethylpyridine is preferably exemplified. In addition, from the viewpoint of obtaining the ester dimer of the present invention in a higher yield, at least one selected from 3,5-lutidine, 3-ethylpyridine, 4-methylpyridine, and 4-ethylpyridine is more preferred.

From the viewpoint of completely neutralizing the oxidizing agent-derived acid to inhibit decomposition of the acetal group of the dioxolane and the ester dimer of the present invention, a molar ratio of the pyridine having an alkyl substituent relative to the dioxolane or the mixture of the dioxolane and the dioxane is preferably 1.0 or more, more preferably 1.1 or more, still more preferably 1.2 or more, and yet still more preferably 1.3 or more. In addition, from the viewpoints of economy and easiness of recovery of the excessive base, the aforementioned molar ratio is preferably 2.5 or less, more preferably 2.0 or less, and still more preferably 1.7 or less.

[Nitroxyl Radical Species]

In the present reaction, as the nitroxyl radical species, a compound selected from an organic nitroxyl radical, an N-hydroxy form thereof, and a salt containing an oxo ammonium cation of them, all of which have oxidative esterification activity against the dioxolane through a combination with an oxidizing agent, is used.

That is, as the nitroxyl radical species, at least one Compound B selected from an organic nitroxyl radical, an N-hydroxy form thereof, and a salt containing an oxo ammonium cation of them is used.

From the viewpoint that high oxidative esterification activity is obtained, Compound B is preferably a compound selected from an organic nitroxyl radical and a salt containing an oxo ammonium cation thereof, and more preferably an N-hydroxy form of an organic nitroxyl radical.

From the viewpoint that high oxidative esterification activity is obtained, the organic nitroxyl radical is preferably a compound represented by the following formula (VIII), a compound represented by the following formula (IX), or a compound represented by the following formula (X). That is, the nitroxyl radical species is preferably a compound selected from a compound represented by the following formula (VIII), a compound represented by the following formula (IX), or a compound represented by the following formula (X), an N-hydroxy form of them, and a salt containing an oxo ammonium cation of them.

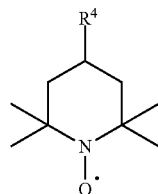

(VIII)

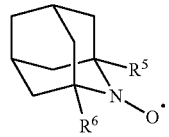

(IX)

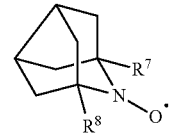

(X)

In the formula (VIII), $R^4$ represents a hydrogen atom, a halogen atom, a hydroxy group, an alkoxy group, an acyloxy group, an alkoxycarbonyl group, an amino group, an acylamino group, a sulfonyloxy group, an N-alkylcarbamoyloxy group, a carboxy group, a cyano group, an isocyanato group, an isothiocyanato group, or an oxo group. In the formula (IX), $R^5$ and $R^6$ each independently represent a hydrogen atom or a methyl group. In the formula (X), $R^7$ and $R^8$ each independently represent a hydrogen atom or a methyl group.

In the formula (VIII), $R^4$ represents a hydrogen atom, a halogen atom, a hydroxy group (—OH), an alkoxy group, an acyloxy group, an alkoxycarbonyl group, an amino group, an acylamino group, a sulfonyloxy group, an N-alkylcarbamoyloxy group, a carboxy group (—C(=O)—OH), a cyano group (—C≡N), an isocyanato group (—N=C=O), an isothiocyanato group (—N=C=S), or an oxo group (=O). In the formula (VIII), from the viewpoint of availability and obtaining the ester dimer of the present invention in a high yield, $R^4$ is preferably an alkoxy group, an acyloxy group, or an acylamino group.

Examples of the halogen atom include a fluorine atom, a chlorine atom, a bromine atom, and an iodine atom, and from the viewpoints of easy availability or preparation and low molecular weight, a fluorine atom, a chlorine atom, or a bromine atom is preferred.

The alkoxy group is represented by —OR$^9$, and R$^9$ represents a monovalent hydrocarbon group. From the viewpoints of easy availability or preparation and low molecular weight, R$^9$ is preferably an alkyl group having 1 to 12 carbon atoms, an alkenyl group having 2 to 12 carbon atoms, an alkynyl group having 2 to 12 carbon atoms, or an aryl group having 6 to 20 carbon atoms; more preferably an alkyl group having 1 to 6 carbon atoms, an alkenyl group having 2 to 6 carbon atoms, an alkynyl group having 2 to 6 carbon atoms, or an aryl group having 6 to 14 carbon atoms; still more preferably an alkyl group having 1 to 4 carbon atoms, an alkenyl group having 2 to 4 carbon atoms, an alkynyl group having 2 to 4 carbon atoms, or an aryl group having 6 to 10 carbon atoms; and yet still more preferably a methyl group. In R$^9$, a part of the hydrogen atoms may be substituted with a halogen atom.

The acyloxy group is represented by —O(C=O)—R$^{10}$. From the viewpoints of easy availability or preparation and low molecular weight, R$^{10}$ is preferably a hydrogen atom, an alkyl group having 1 to 12 carbon atoms, an alkenyl group having 1 to 12 carbon atoms, or an aryl group having 6 to 20 carbon atoms; more preferably a hydrogen atom, an alkyl group having 1 to 8 carbon atoms, or an aryl group having 6 to 14 carbon atoms; still more preferably a hydrogen atom, an alkyl group having 1 to 4 carbon atoms, or an aryl group having 6 to 10 carbon atoms; yet still more preferably a methyl group, an ethyl group, or a phenyl group; and even yet still more preferably a phenyl group.

The acylamino group is represented by —NH(C=O)—R$^{11}$. From the viewpoints of easy availability or preparation and low molecular weight, R$^{11}$ is preferably a hydrogen atom, an alkyl group having 1 to 12 carbon atoms, or an aryl group having 6 to 20 carbon atoms; more preferably a hydrogen atom, an alkyl group having 1 to 8 carbon atoms, or an aryl group having 6 to 14 carbon atoms; still more preferably a hydrogen atom, an alkyl group having 1 to 4 carbon atoms, or an aryl group having 6 to 10 carbon atoms; yet still more preferably a methyl group, an ethyl group, or a phenyl group; and even yet still more preferably a methyl group.

The sulfonyloxy group is represented by —O(O=S=O)—R$^{12}$. From the viewpoints of easy availability or preparation and low molecular weight, R$^{12}$ is preferably an alkyl group having 1 to 12 carbon atoms or an aryl group having 6 to 20 carbon atoms; more preferably an alkyl group having 1 to 8 carbon atoms or an aryl group having 6 to 14 carbon atoms; still more preferably an alkyl group having 1 to 4 carbon atoms or an aryl group having 6 to 10 carbon atoms; yet still more preferably a methyl group, an ethyl group, or a p-tolyl group; and even yet still more preferably a methyl group or a p-tolyl group.

Specifically, examples of the nitroxyl radical species include TEMPO, 4-hydroxy-TEMPO, 4-amino-TEMPO, 4-methoxy-TEMPO (hereinafter also referred to as "4-OMe-TEMPO"), 4-ethoxy-TEMPO, 4-phenoxy-TEMPO, 4-acetoxy-TEMPO, 4-benzoyloxy-TEMPO (hereinafter also referred to as "4-OBz-TEMPO"), 4-methacrylate-TEMPO, 4-acetamido-TEMPO (hereinafter also referred to as "4-NHAc-TEMPO"), 4-methylsulfonyloxy-TEMPO (hereinafter also referred to as "4-OMs-TEMPO"), 4-p-toluenesulfonyloxy-TEMPO, 4-oxo-TEMPO, 2-azaadamantane-N-hydroxyl (hereinafter also referred to as "AZADOL" (a trademark, manufactured by Nissan Chemical Industries, Ltd.)), 2-azaadamantane-N-oxyl (hereinafter also referred to as "AZADO"), 1-methyl-2-azaadamantane-N-oxyl (hereinafter also referred to as "1-Me-AZADO"), 9-azanoradamantane-N-oxyl (hereinafter also referred to as "nor-AZADO"), and 1,5-dimethyl-9-azanoradamantane-N-oxyl (hereinafter also referred to as "DMM-AZADO").

From the viewpoints of availability and obtaining the ester dimer of the present invention in a high yield, the nitroxyl radical species is preferably a compound selected from 4-methoxy-TEMPO, 4-benzoyloxy-TEMPO, 4-acetamido-TEMPO, 4-methylsulfonyloxy-TEMPO, and AZADOL, and more preferably a compound selected from 4-benzoyloxy-TEMPO, 4-acetamido-TEMPO, 4-methylsulfonyloxy-TEMPO, and AZADOL.

Though preferred compounds are hereunder exemplified, in the present invention, it should be construed that the nitroxyl radical species is not limited to these compounds.

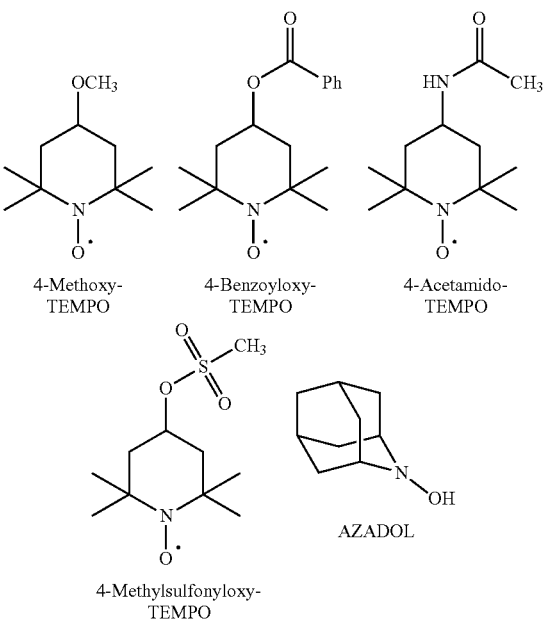

From the viewpoint of securing satisfactory oxidation activity, a use amount of the compound selected from an organic nitroxyl radical, an N-hydroxy form thereof, and a salt containing an oxo ammonium cation of them is preferably 0.0001 or more in a molar ratio, more preferably 0.0002 or more in a molar ratio, and still more preferably 0.0005 or more in a molar ratio relative to the dioxolane or the mixture of the dioxolane and dioxane. In addition, from the viewpoint of economy, it is preferably 0.1 or less in a molar ratio, more preferably 0.05 or less in a molar ratio, and still more preferably 0.02 or less in a molar ratio.

[Oxidizing Agent]

In the present reaction, from the viewpoint of reactivity, an oxidizing agent is used together with the nitroxyl radical species. Any oxidizing agent capable of oxidizing the organic nitroxyl radical or an N-hydroxy form thereof into an oxo ammonium cation can be used as the oxidizing agent, and from the viewpoint of suppressing a lowering of the yield due to hydration or hydrolysis of the ester dimer of the present invention, an oxidizing agent composed of a compound containing a halogen, which is capable of being used in an organic solvent (hereinafter also referred to as "halogen-containing oxidizing agent"), is preferred. Examples of the halogen-containing oxidizing agent include an oxidizing agent composed of a compound containing chlorine (hereinafter also referred to as "chlorine-containing oxidizing agent"), such as sodium hypochlorite pentahydrate, metachloroperbenzoic acid, trichloroisocyanuric acid (hereinafter also referred to as "TCCA"), tertiary butyl hypochlorite (hereinafter also referred to as "tBuOCl"), and N-chlorosuccinimide; an oxidizing agent composed of a compound containing bromine (hereinafter also referred to as "bromine-containing oxidizing agent"), such as N-bromosuccinimide; and a halogen-containing oxidizing agent having plural halogen elements, such as (dichloroiodo) benzene. From the viewpoint of obtaining the ester dimer of the present invention in a high yield and the viewpoints of stability, safety, and easiness of handling of the oxidizing agent, the halogen-containing oxidizing agent is preferably a chlorine-containing oxidizing agent, and more preferably an oxidizing agent selected from TCCA and tBuOCl, with TCCA being still more preferred from the viewpoint of availability.

As the oxidizing agent of the present invention, an oxoammonium cation of an organic nitroxyl radical or an N-hydroxy form thereof, including an oxoammonium cation resulting from one electron oxidation of the compound represented by the formula (VIII), the compound represented by the formula (IX), or the compound represented by the formula (X), is excluded.

From the viewpoints of making both high reaction conversion of the dioxolane or the mixture of the dioxolane and the dioxane and suppression of production amount of the formyl dioxolane compatible with each other, a molar ratio of the oxidation active species relative to the dioxolane or the mixture of the dioxolane and the dioxane is preferably 1.0 or more, and more preferably 1.1 or more. In addition, from the viewpoints of economy and reduction of waste amount, the molar ratio is preferably 2.0 or less, and more preferably 1.5 or less.

The oxidation active species means a chlorine atom in the case of the chlorine-containing oxidizing agent, and in the case of TCCA, 3 moles of the oxidation active species is existent in one mole of the molecule.

[Solvent]

In the present reaction, it is possible to carry out the reaction under a non-solvent or solvent-used condition. In the case where the oxidizing agent to be used or an oxidizing agent-derived reduced product or salt, which is by-produced at the time of reaction, is a solid, from the viewpoints of dissolving the solid and decreasing the viscosity of the reaction solution to make it easy to perform stirring, the solvent-used condition is preferred. Any solvent can be used so far as it is inert against the dioxolane or the mixture of the dioxane and the dioxolane, the oxidizing agent, and the base, and in the case of using TCCA as the oxidizing agent, from the viewpoint of solubility of TCCA and availability, a solvent selected from acetone, 2-butanone, cyclopentanone, acetonitrile, and dichloromethane is preferred; a solvent selected from acetone, 2-butanone, acetonitrile, and dichloromethane is more preferred; and a solvent selected from acetone and 2-butanone is still more preferred. In addition, from the viewpoint of productivity of the ester dimer of the present invention, acetonitrile is still more preferred.

The solvent may be used alone or may be used in combination of two or more thereof.

The use amount of the solvent is not particularly limited, and from the viewpoint of operability, the use amount of the solvent relative to the whole of the reaction system is preferably 20% by mass or more, more preferably 30% by mass or more, still more preferably 40% by mass or more, yet still more preferably 50% by mass or more, and even yet still more preferably 60% by mass or more, and from the viewpoint of productivity, the use amount of the solvent relative to the whole of the reaction system is preferably 90% by mass or less, more preferably 85% by mass or less, and still more preferably 80% by mass or less.

[Reaction Procedures]

In the present reaction, the charging order of the respective raw materials, and the like are not limited, since the reaction is an exothermic oxidation reaction, from the viewpoints of easiness of temperature control of the reaction solution and safety, a method of dropping the oxidizing agent or oxidizing agent solution to the mixture or the mixed solution containing the raw materials other than the oxidizing agent is preferred.

From the viewpoint of suppressing a facility load and a rise of viscosity of the reaction solution, a temperature of the reaction solution during dropping of the oxidizing agent or oxidizing agent solution is preferably −15° C. or higher, and more preferably −10° C. or higher. In addition, from the viewpoint of suppressing a side-reaction, such as decomposition at a high temperature, to obtain the ester dimer of the present invention in a high yield, the temperature of the reaction solution is preferably 25° C. or lower, and more preferably 10° C. or lower. After completion of dropping of the oxidizing agent or oxidizing agent solution, the reaction is continued until the dioxolane all react, or a lowering of the residual amount stops. From the viewpoint of promoting the reaction of the dioxolane, the temperature of the reaction solution is preferably −10° C. or higher, and more preferably −5° C. or higher, and from the viewpoint of suppressing a side-reaction, it is preferably 50° C. or lower, and more preferably 30° C. or lower.

At the time of completion of the reaction, from the viewpoints of suppression of a side-reaction and safety, it is preferred to add a reaction terminator that completely consumes the residual oxidizing agent. As the reaction terminator, any compound can be used so far as it reacts with the oxidizing agent and hardly reacts with the oxidation product, such as the ester dimer of the present invention, and; however, from the viewpoints of availability and making it easy to purify the ester dimer of the present invention, an alcohol is preferred. The alcohol is preferably a primary or secondary alcohol, and from the viewpoint of suppressing ester interchange with the ester dimer of the present invention, the alcohol is more preferably a secondary alcohol. In addition, an alcohol having 1 or more and 12 or less carbon atoms is preferred.

The addition amount of the reaction terminator is not particularly limited.

[Separation of Compound Represented by Formula (II) and Recovery of Pyridine Having Alkyl Substituent]

In the present invention, it is preferred to include a step of, after the step of oxidatively esterifying the dioxolane, or preferably the mixture of dioxolane and dioxane, separating the ester dimer of the present invention (compound represented by the formula (II)).

In the step of separating the ester dimer of the present invention, from the viewpoint of efficiency, it is preferred that the solid, such as the salt or the reduced product of the oxidizing agent, is separated by means of filtration or oil-water extraction, and the dioxanone, the formyl dioxolane, and the residual base are separated by means of distillation or column chromatography.

For the separation between the dioxanone and the ester dimer of the present invention, from the viewpoint of making it possible to easily perform the separation utilizing a large difference in boiling point, the separation by means of distillation is more preferred. It is possible to carry out the separation by means of distillation under either simple distillation conditions or rectification conditions, and from the viewpoint of obtaining the high-purity ester dimer of the present invention in a high distillation yield, it is preferred to perform the separation under rectification conditions. As for the rectification conditions, from the viewpoint of highly purifying the ester dimer of the present invention, the number of theoretical stages of a rectifying tower is preferably 2 stages or more, and more preferably 5 stages or more, and a reflux ratio is preferably 0.1 or more, and more preferably 0.5 or more. In addition, from the viewpoint of purification productivity of the ester dimer of the present invention, the number of theoretical stages of the rectifying tower is preferably 20 stages or less, and more preferably 10 stages or less, and the reflux ratio is preferably 20 or less, and more preferably 10 or less.

In the production method of the present invention, the pyridine having an alkyl substituent can be easily recovered after the reaction through extraction with an organic solvent, or the like.

The novel glyceric acid ester of the present invention (ester dimer of the present invention) is a glyceric acid ester in which hydroxy groups at the 2-position and 3-position are protected as a cyclic acetal group and is useful as synthetic intermediates for glyceric acid, a glyceric acid salt, a deprotected glyceric acid ester, and the like, which are used as raw materials for various medicaments, cosmetics, detergents, polymers and the like.

[Production Method of Glyceric Acid, Glyceric Acid Salt, or Deprotected Glyceric Acid Ester]

Glyceric acid, a glyceric acid salt, or a deprotected glyceric acid ester can be produced through hydrolysis or alcoholysis of the acetal group and the ester group of the above-obtained ester dimer of the present invention. Though the hydrolysis or alcoholysis method is not particularly limited, a method of performing the decomposition with an excessive amount of water or an alcohol in the presence of an acid catalyst is the easiest and preferred.

The alcohol which is used for the alcoholysis is preferably a primary alcohol from the viewpoint of reactivity (in particular, decomposition of the acetal group), and more preferably a primary alcohol having 1 or more and 3 or less carbon atoms from the viewpoint that a boiling point of the deprotected glyceric acid ester is low and readily subjected to distillation purification.

From the viewpoint that the polarity of the deprotected glyceric acid ester is thoroughly decreased, thereby allowing the deprotected glyceric acid ester and glycerin to be readily separated and purified by an oil-water extraction method, a linear or branched primary alcohol having 4 or more and 8 or less carbon atoms is more preferred.

The resulting glyceric acid, glyceric acid salt, or deprotected glyceric acid ester is separated from the by-product (glycerin, aldehyde, or an acetal thereof) preferably by means of distillation, column chromatography, or the like.

The present invention further discloses the following [1] to [39].

[1] A method of producing a compound represented by the following formula (II), including a step of oxidatively esterifying Compound A represented by the following formula (I) with Compound B selected from an organic nitroxyl radical, an N-hydroxy form thereof, and a salt containing an oxo ammonium cation of them, and an oxidizing agent in the presence of a pyridine having an alkyl substituent, wherein the use amount of Compound B is 0.0001 or more and 0.1 or less in terms of a molar ratio relative to Compound A.

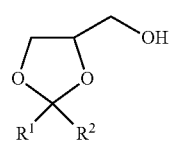

In the formula (I), $R^1$ and $R^2$ each independently represent a hydrogen atom or a monovalent hydrocarbon group, or $R^1$ and $R^2$ are bonded to each other to form a divalent hydrocarbon group for constituting a ring structure.

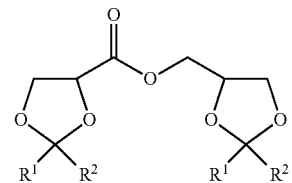

In the formula (II), $R^1$ and $R^2$ each independently represent a hydrogen atom or a monovalent hydrocarbon group, or $R^1$ and $R^2$ are bonded to each other to form a divalent hydrocarbon group for constituting a ring structure.

[2] The production method as set forth in [1], wherein the number of alkyl substituent of the pyridine having an alkyl substituent is preferably 1 to 4, more preferably 1 to 3, and still more preferably 1 or 2.

[3] The production method as set forth in [1] or [2], wherein the alkyl substituent of the pyridine having an alkyl substituent each independently has preferably 1 or more carbon atoms, preferably 12 or less carbon atoms, more preferably 10 or less carbon atoms, still more preferably 8 or less carbon atoms, yet still more preferably 6 or less carbon atoms, even yet still more preferably 4 or less carbon atoms, and even still more preferably 2 or less carbon atoms.

[4] The production method as set forth in any of [1] to [3], wherein the alkyl substituent of the pyridine having an alkyl substituent may be linear, branched, or cyclic, it is preferably linear or branched, and more preferably linear.

[5] The production method as set forth in any of [1] to [4], wherein the pyridine having an alkyl substituent is a pyridine having an alkyl substituent at at least one position selected from the 3-position, the 4-position, and the 5-position, and preferably a pyridine having an alkyl substituent at at least one position selected from the 3-position, the 4-position, and the 5-position and not having an alkyl substituent at the 2-position and the 6-position.

[6] The production method as set forth in any of [1] to [5], wherein the pyridine having an alkyl substituent is preferably 2-methylpyridine, 3-methylpyridine, 4-methylpyridine, 2-ethylpyridine, 3-ethylpyridine, 4-ethylpyridine, 2-propylpyridine, 3-propylpyridine, 4-propylpyridine, 3-n-butylpyridine, 4-tert-butylpyridine, 2-amylpyridine, 4-amylpyridine, 2-(3-pentyl)pyridine, 4-(3-penyl)pyridine, 2,3-lutidine (another name: 2,3-dimethylpyridine), 2,4-lutidine (another name: 2,4-dimethylpyridine), 2,5-lutidine (another name: 2,5-dimethylpyridine), 2,6-lutidine (another name: 2,6-dimethylpyridine), 3,4-lutidine (another name: 3,4-dimethylpyridine), 3,5-lutidine (another name: 3,5-dimethylpyridine), 5-ethyl-2- methylpyridine, 2,6-di-tert-butylpyridine, 2,3,5-collidine (another name: 2,3,5-trimethylpyridine), or 2,4,6-collidine (another name: 2,4,6-trimethylpyridine); more preferably at least one selected from 5-ethyl-2-methylpyridine, 3,5-lutidine, 2,6-lutidine, 3-ethylpyridine, 4-methylpyridine, and 4-ethylpyridine; and still more preferably at least one selected from 3,5-lutidine, 3-ethylpyridine, 4-methylpyridine, and 4-ethylpyridine.

[7] The production method as set forth in any of [1] to [6], wherein a molar ratio of the pyridine having an alkyl substituent relative to the dioxolane or the mixture of the dioxolane and the dioxane is preferably 1.0 or more, more preferably 1.1 or more, still more preferably 1.2 or more, and yet still more preferably 1.3 or more, and the aforementioned molar ratio is preferably 2.5 or less, more preferably 2.0 or less, and still more preferably 1.7 or less.

[8] The production method as set forth in any of [1] to [7], wherein in the formulae (I) and (II), preferably, $R^1$ is a hydrogen atom, and $R^2$ is a hydrogen atom or a monovalent hydrocarbon atom; more preferably, $R^1$ is a hydrogen atom, and $R^2$ is a hydrogen atom or a monovalent hydrocarbon atom having 1 or more and 20 or less carbon atoms; the hydrocarbon group for $R^2$ is preferably an alkyl group or an aryl group; the carbon number of this alkyl group is preferably 1 or more, and it is preferably 20 or less, more preferably 18 or less, still more preferably 16 or less, yet still more preferably 14 or less, yet still more preferably 12 or less, yet still more preferably 10 or less, yet still more preferably 8 or less, yet still more preferably 6 or less, yet still more preferably 4 or less, and yet still more preferably 2 or less; such an alkyl group may be either linear or branched; the carbon number of the aryl group for $R^2$ is preferably 6 or more, and it is preferably 20 or less, more preferably 18 or less, still more preferably 16 or less, yet still more preferably 14 or less, yet still more preferably 12 or less, yet still more preferably 10 or less, yet still more preferably 8 or less, and yet still more preferably 6 or less; and $R^2$ is more preferably a hydrogen atom, a linear alkyl group having 1 or more and 8 or less carbon atoms, a branched alkyl group having 1 or more and 8 or less carbon atoms, or an aryl group having 6 or more and 14 or less carbon atoms, still more preferably a hydrogen atom, a methyl group, or a phenyl group, and yet still more preferably a hydrogen atom.

[9] The production method as set forth in any of [1] to [7], wherein in the formulae (I) and (II), preferably, $R^1$ and $R^2$ are each a monovalent hydrocarbon group; more preferably, $R^1$ is a monovalent hydrocarbon group having 1 or more and 8 or more carbon atoms, and $R^2$ is a monovalent hydrocarbon group having 2 or more and 8 or less carbon atoms; still more preferably, $R^1$ is an alkyl group having 1 or more and 8 or less carbon atoms, and $R^2$ is an alkyl group having 2 or more and 8 or less carbon atoms: yet still more preferably, $R^1$ is an alkyl group having 1 or 2 carbon atoms, and $R^2$ is an alkyl group having 2 or more and 6 or less carbon atoms; yet still more preferably, $R^1$ is an alkyl group having 1 or 2 carbon atoms, and $R^2$ is an alkyl group having 2 or more and 4 or less carbon atoms; and yet still more preferably, $R^1$ is a methyl group and $R^2$ is an ethyl group or $R^1$ and $R^2$ are bonded to each other to form a divalent hydrocarbon group for constituting a ring structure. $R^1$ and $R^2$ are preferably bonded to each other to form a divalent hydrocarbon group having 2 or more and 7 or less carbon atoms, more preferably a divalent hydrocarbon group having 3 or more and 6 or less carbon atoms, still more preferably a divalent hydrocarbon group having 4 or more and 5 or less carbon atoms, and yet still more preferably a divalent hydrocarbon group having 5 carbon atoms; the ring structure containing $R^1$ and $R^2$ is preferably a 3- to 8-membered ring, more preferably a 4- to 7-membered ring, still more preferably a 5- to 6-membered ring, and yet still more preferably a 6-membered ring; and the ring structure containing $R^1$ and $R^2$ is preferably a cycloalkane structure, more preferably a ring structure having 5 or 6 carbon atoms (cyclopentane ring or cyclohexane ring), and still more preferably a cyclohexane ring.

[10] The production method as set forth in any of [1] to [9], including a step of oxidatively esterifying a mixture of a compound represented by the following formula (I) and a compound represented by the following formula (V).

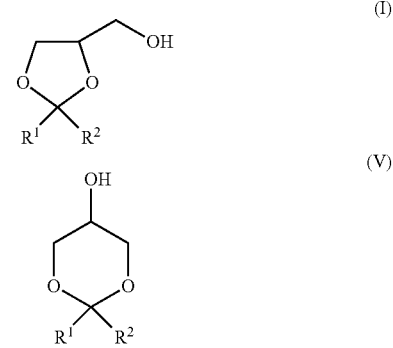

In the formulae (I) and (V), $R^1$ and $R^2$ each independently represent a hydrogen atom or a monovalent hydrocarbon group, or $R^1$ and $R^2$ are bonded to each other to form a divalent hydrocarbon group for constituting a ring structure.

[11] The production method as set forth in any of [1] to [10], wherein the compound represented by the formula (I) is produced by a method of acetalizing glycerol and a compound represented by the following formula (III) in the presence of an acid catalyst (method 1), or subjecting glycerol and a compound represented by the formula (IV) to acetal exchange in the presence of an acid catalyst (method 2).

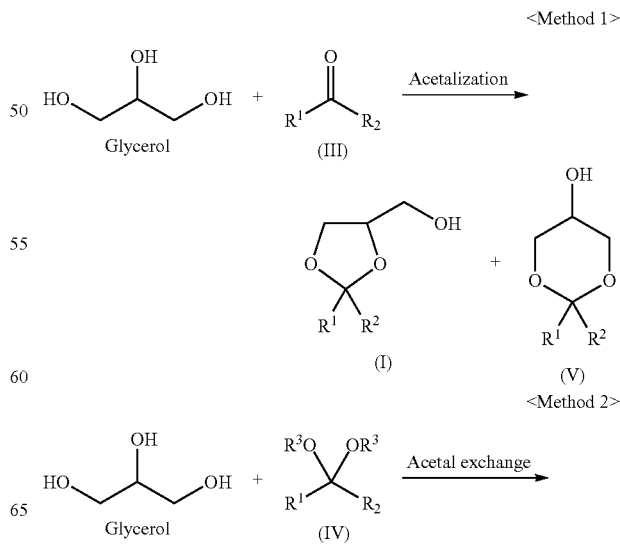

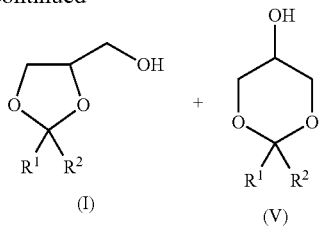

In the formulae (III) and (IV), $R^1$ and $R^2$ each independently represent a hydrogen atom or a monovalent hydrocarbon group, or $R^1$ and $R^2$ are bonded to each other to form a divalent hydrocarbon group for constituting a ring structure. In the formula (IV), $R^3$'s each independently represent a monovalent hydrocarbon group, preferably a group selected from hydrocarbon groups having 1 or more and 8 or less carbon atoms, more preferably a monovalent hydrocarbon group having 1 or more and 3 or less carbon atoms, still more preferably a monovalent alkyl group having 1 or more and 3 or less carbon atoms, and yet still more preferably a methyl group.

[12] The production method as set forth in any of [1] to [11], including the following step 1 and step 2.

Step 1: A step of acetalizing glycerol and a compound represented by the following formula (III) or a polymer thereof in the presence of an acid catalyst (step 1-1), or a step of subjecting glycerol and a compound represented by the following formula (IV) to acetal exchange in the presence of an acid catalyst (step 1-2)

Step 2: A step of oxidatively esterifying a mixture of a compound represented by the following formula (I) and a compound represented by the following formula (V)

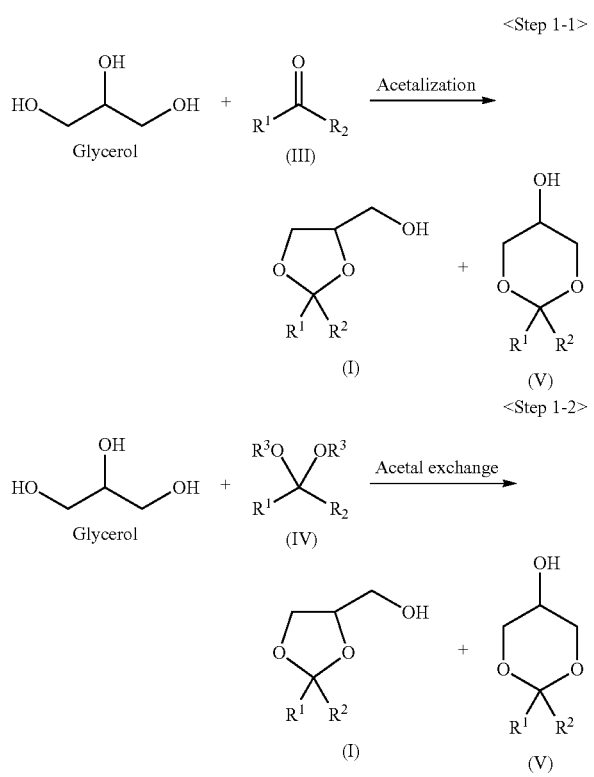

In the formulae, $R^1$ and $R^2$ each independently represent a hydrogen atom or a monovalent hydrocarbon group, or $R^1$ and $R^2$ are bonded to each other to form a divalent hydrocarbon group for constituting a ring structure, provided that the case where $R^1$ and $R^2$ are a methyl group at the same time is excluded; and $R^3$'s each independently represent a monovalent hydrocarbon group, preferably a hydrocarbon group having 1 or more and 8 or less carbon atoms, more preferably a monovalent hydrocarbon group having 1 or more and 3 or less carbon atoms, still more preferably a monovalent alkyl group having 1 or more and 3 or less carbon atoms, and yet still more preferably a methyl group.

[13] The production method as set forth in [11] or [12], wherein in the formulae (III) and (IV), preferably, $R^1$ and $R^2$ are each a hydrogen atom or a group selected from monovalent hydrocarbon groups having 1 or more and 20 or less carbon atoms, or $R^1$ and $R^2$ are bonded to each other to form a divalent hydrocarbon group for constituting a ring structure having 5 or more and 8 or less carbon atoms.

[14] The production method as set forth in any of [11] to [13], wherein in the formulae (III) and (IV), preferably, $R^1$ is a hydrogen atom, and $R^2$ is a hydrogen atom or a monovalent hydrocarbon group; more preferably, $R^1$ is a hydrogen atom, and $R^2$ is a hydrogen atom or a monovalent hydrocarbon atom having 1 or more and 20 or less carbon atoms; the hydrocarbon group for $R^2$ is preferably an alkyl group or an aryl group; the carbon number of this alkyl group is preferably 1 or more, and it is preferably 20 or less, more preferably 18 or less, still more preferably 16 or less, yet still more preferably 14 or less, yet still more preferably 12 or less, yet still more preferably 10 or less, yet still more preferably 8 or less, yet still more preferably 6 or less, yet still more preferably 4 or less, and yet still more preferably 2 or less; such an alkyl group may be either linear or branched; the carbon number of the aryl group for $R^2$ is preferably 6 or more, and it is preferably 20 or less, more preferably 18 or less, still more preferably 16 or less, yet still more preferably 14 or less, yet still more preferably 12 or less, yet still more preferably 10 or less, yet still more preferably 8 or less, and yet still more preferably 6 or less; and $R^2$ is more preferably a hydrogen atom, a linear alkyl group having 1 or more and 8 or less carbon atoms, a branched alkyl group having 1 or more and 8 or less carbon atoms, or an aryl group having a carbon umber of 6 or more and 14 or less, still more preferably a hydrogen atom, a methyl group, or a phenyl group, and yet still more preferably a hydrogen atom.

[15] The production method as set forth in any of [11] to [13], wherein in the formulae (III) and (IV), preferably, $R^1$ is a monovalent hydrocarbon group having 1 or more and 8 or more carbon atoms, and $R^2$ is a monovalent hydrocarbon group having 2 or more and 8 or less carbon atoms; more preferably, $R^1$ is an alkyl group having 1 or more and 8 or less carbon atoms, and $R^2$ is an alkyl group having 2 or more and 8 or less carbon atoms; still more preferably, $R^1$ is an alkyl group having 1 or 2 carbon atoms, and $R^2$ is an alkyl group having 2 or more and 6 or less carbon atoms; yet still more preferably, $R^1$ is an alkyl group having 1 or 2 carbon atoms, and $R^2$ is an alkyl group having 2 or more and 4 or less carbon atoms; yet still more preferably, $R^1$ is a methyl group and $R^2$ is an ethyl group or $R^1$ and $R^2$ are bonded to each other to form a divalent hydrocarbon group for constituting a ring structure. $R^1$ and $R^2$ are preferably bonded to each other to form a divalent hydrocarbon group having 2 or more and 7 or less carbon atoms, more preferably a divalent hydrocarbon group having 3 or more and 6 or less carbon atoms, still more preferably a divalent hydrocarbon group having 4 or more and 5 or less carbon atoms, and yet still more preferably a divalent hydrocarbon group having 5 carbon atoms; the ring structure containing $R^1$ and $R^2$ is preferably a 3- to 8-membered ring, more preferably a 4- to 7-membered ring, still more preferably a 5- to 6-membered ring, and yet still more preferably a 6-membered ring; and the ring structure containing $R^1$ and $R^2$ is preferably a cycloalkane structure, more preferably a ring structure having 5 or 6 carbon atoms (cyclopentane ring or cyclohexane ring), and still more preferably a cyclohexane ring.

[16] The production method as set forth in any of [1] to [15], wherein Compound B is a compound selected from an organic nitroxyl radical and a salt containing an oxo ammonium cation thereof.

[17] The production method as set forth in any of [1] to [16], wherein the organic nitroxyl radical is a compound represented by the following formula (VIII), a compound represented by the following formula (IX), or a compound represented by the following formula (X).

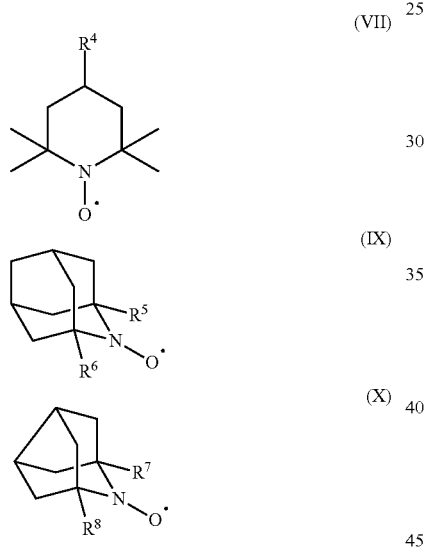

In the formula (VIII), $R^4$ represents a hydrogen atom, a halogen atom, a hydroxy group, an alkoxy group, an acyloxy group, an alkoxycarbonyl group, an amino group, an acylamino group, a sulfonyloxy group, an N-alkylcarbamoyloxy group, a carboxy group, a cyano group, an isocyanate group, an isothiocyanate group, or an oxo group, and preferably an alkoxy group, an acyloxy group, or an acylamino group. In the formula (IX), $R^5$ and $R^6$ each independently represent a hydrogen atom or a methyl group. In the formula (X), $R^7$ and $R^8$ each independently represent a hydrogen atom or a methyl group.

[18] The production method as set forth in any of [1] to [15], wherein Compound B is an N-hydroxy form of an organic nitroxyl radical.

[19] The production method as set forth in any of [1] to [18], wherein at least one compound selected from the organic nitroxyl radical, an N-hydroxy form thereof, and a salt containing an oxo ammonium cation of them is preferably TEMPO, 4-hydroxyTEMPO, 4-amino-TEMPO, 4-methoxy-TEMPO (hereinafter also referred to as "4-OMe-TEMPO"), 4-ethoxy-TEMPO, 4-phenoxy-TEMPO, 4-acetoxy-TEMPO, 4-benzoyloxy-TEMPO (hereinafter also referred to as "4-OBz-TEMPO"), 4-methacrylate-TEMPO, 4-acetamido-TEMPO (hereinafter also referred to as "4-NHAc-TEMPO"), 4-methylsulfonyloxy-TEMPO (hereinafter also referred to as "4-OMs-TEMPO"), 4-p-toluenesulfonyloxy-TEMPO, 4-oxo-TEMPO, 2-azaadamantane-N-hydroxy (hereinafter also referred to as "AZADOL"), 2-azaadamantane-N-oxyl (hereinafter also referred to as "AZADO"), 1-methyl-2-azaadamantane-N-oxyl (hereinafter also referred to as "1-Me-AZADO"), 9-azanoradamantane-N-oxyl (hereinafter also referred to as "nor-AZADO"), or 1,5-dimethyl-9-azanoradamantane-N-oxyl (hereinafter also referred to as "DMM-AZADO"); more preferably a compound selected from 4-methoxy-TEMPO, 4-benzoyloxy-TEMPO, 4-acetamido-TEMPO, 4-methylsulfonyloxy-TEMPO, and AZADOL; and still more preferably a compound selected from 4-benzoyloxy-TEMPO, 4-acetamido-TEMPO, 4-methylsulfonyloxy-TEMPO, and AZADOL.

[20] The production method as set forth in any of [1] to [19], wherein the use amount of Compound B selected from the organic nitroxyl radical, an N-hydroxy form thereof, and a salt containing an oxo ammonium cation of them is 0.0001 or more in a molar ratio, more preferably 0.0002 or more in a molar ratio, and still more preferably 0.0005 or more in a molar ratio, and it is 0.1 or less in a molar ratio, more preferably 0.05 or less in a molar ratio, and still more preferably 0.02 or less in a molar ratio, relative to the compound represented by the formula (I) or Compound A represented by the formula (I).

[21] The production method as set forth in any of [1] to [20], wherein the oxidizing agent is preferably an oxidizing agent composed of a compound containing a halogen (halogen-containing oxidizing agent), more preferably an oxidizing agent composed of a compound containing chlorine (chlorine-containing oxidizing agent), still more preferably an oxidizing agent selected from trichloroisocyanuric acid and tertiary butyl hypochlorite, and yet still more preferably trichloroisocyanuric acid.

[22] The production method as set forth in any of [1] to [21], wherein a molar ratio of the oxidation active species of the oxidizing agent relative to the compound represented by the formula (I) or the mixture of the compound represented by the formula (I) and the compound represented by the formula (V) is preferably 1.0 or more, and more preferably 1.1 or more, and it is preferably 2.0 or less, and more preferably 1.5 or less.

[23] The production method as set forth in any of [1] to [22], wherein a molar ratio of the pyridine having an alkyl substituent relative to the compound represented by the formula (I) or the mixture of the compound represented by the formula (I) and the compound represented by the formula (V) is preferably 1.0 or more, more preferably 1.1 or more, still more preferably 1.2 or more, and yet still more preferably 1.3 or more, and the molar ratio is preferably 2.5 or less, more preferably 2.0 or less, and still more preferably 1.7 or less.

[24] The production method as set forth in any of [1] to [23], wherein in the step of oxidatively esterifying the compound represented by the formula (I), a solvent is preferably used, and the solvent is preferably a solvent selected from acetone, 2-butanone, cyclopentanone, acetonitrile, and dichloromethane; more preferably a solvent selected from acetone, 2-butanone, acetonitrile, and dichloromethane; still more preferably a solvent selected from acetone and 2-butanone; and yet still more preferably acetonitrile.

[25] The production method as set forth in [24], wherein the use amount of the solvent relative to the whole of the reaction system is preferably 20% by mass or more, more preferably 30% by mass or more, still more preferably 40% by mass or more, yet still more preferably 50% by mass or more, and even yet still more preferably 60% by mass or more, and it is preferably 90% by mass or less, more preferably 85% by mass or less, and still more preferably 80% by mass or less.

[26] The production method as set forth in any of [1] to [25], wherein in the step of oxidatively esterifying the compound represented by the formula (I) or the mixture of the compound represented by the formula (I) and the compound represented by the formula (V), the oxidizing agent or oxidizing agent solution is preferably dropped in the mixture or the mixed solution containing the raw materials other than the oxidizing agent.

[27] The production method as set forth in [26], wherein a temperature of the reaction solution during dropping of the oxidizing agent or oxidizing agent solution is preferably −15° C. or higher, and more preferably −10° C. or higher, and it is preferably 25° C. or lower, and more preferably 10° C. or lower.

[28] The production method as set forth in [26] or [27], wherein after completion of dropping of the oxidizing agent or oxidizing agent solution, the reaction is continued until the dioxolane all reacts, or a lowering of the residual amount stops.

[29] The production method as set forth in [28], wherein the temperature of the reaction solution is preferably −10° C. or higher, and more preferably −5° C. or higher, and it is preferably 50° C. or lower, and more preferably 30° C. or lower.

[30] The production method as set forth in any of [1] to [29], wherein an alcohol is preferably used as a reaction terminator.

[31] The production method as set forth in [30], wherein the reaction terminator is preferably a primary or secondary alcohol, and more preferably a secondary alcohol.

[32] The production method as set forth in [30] or [31], wherein the reaction terminator is preferably an alcohol having 1 or more and 12 or less carbon atoms.

[33] The production method as set forth in any of [1] to [32], wherein the method includes, after the step of oxidatively esterifying the compound represented by the formula (I), or preferably the mixture of the compound represented by the formula (I) and the compound represented by the formula (V), a step of separating the compound represented by the formula (II) (step 3).

[34] The production method as set forth in [33], wherein the separation in the step 3 is separation through distillation.

[35] The production method as set forth in [34], wherein the separation through distillation is preferably performed under rectification conditions.

[36] The production method as set forth in [35], wherein as for the rectification conditions, the number of theoretical stages of a rectifying tower is preferably 2 stages or more, and more preferably 5 stages or more, and a reflux ratio is preferably 0.1 or more, and more preferably 0.5 or more; and the number of theoretical stages of the rectifying tower is preferably 20 stages or less, and more preferably 10 stages or less, and the reflux ratio is preferably 20 or less, and more preferably 10 or less.

[37] A method of producing glyceric acid, a glyceric acid salt, or a deprotected glyceric acid ester, including subjecting the compound represented by the formula (II) as separated in any of [33] to [36] to hydrolysis or alcoholysis.

[38] The production method as set forth in [37], wherein the alcohol to be used for the alcoholysis is preferably a primary alcohol, and more preferably a primary alcohol having 1 or more and 3 or less carbon atoms

[39] The production method as set forth in [37], wherein the alcohol to be used for the alcoholysis is more preferably a linear or branched primary alcohol having 4 or more and 8 or less carbon atoms.

EXAMPLES

[Identification of Compound]

Each of compounds obtained in the following Production Examples, Examples, or Comparative Examples (hereinafter also referred to as "Examples and the like") was identified through spectral analysis with a nuclear magnetic resonance apparatus (NMR, manufactured by Agilent Technologies, model: Agilent 400-MR DD2), an infrared spectrophotometer (IR, manufactured by Horiba, Ltd., model: FT-710), and a gas chromatography mass spectrometer (GC-MS, manufactured by Agilent Technologies, model: Agilent 5975C).

[Purity of Compound Produced or Purified]

The purity of each of compounds produced or purified in the following Examples and the like was determined through analysis (GC analysis) with a gas chromatograph (manufactured by Agilent Technologies, model: Agilent 6850). The term "%" regarding the purity means "GC %", and this value was used at the time of expressing in terms of a net quantity regarding the reaction raw materials and high-purity authentic samples.

[Unit, Conversion, and Yield]

The conversion of each of reaction raw materials and the yield of each of products shown in the following Examples and the like were determined through internal standard method quantitative GC analysis. A calibration curve necessary for the quantitative analysis was prepared using a commercially available authentic sample, or a high-purity authentic sample purified from a reaction mixture through distillation or silica gel column chromatography. However, the yield of a formyl dioxolane was calculated by substituting a calibration curve of a corresponding dioxanone.

[Measurement Conditions of GC and GC-MS]

Column: Ultra ALLOY-1 (MS/HT) (Frontier Laboratories Ltd. a trademark, inner diameter: 0.25 mm, film thickness: 0.15 μm, length: 30 m)

Carrier gas: Helium, 1.0 mL/min

Injection conditions: 250° C., split ratio: 1/50

Detection conditions: FID system, 220° C.

Column temperature conditions: After holding at 40° C. for 5 minutes, the temperature is raised to 350° C. at 10° C./min.

Internal standard compound: n-Dodecane

Ionization mode: EI

Ion source temperature: 230° C.

Interface temperature: 350° C.

Production Examples: Production of 2,2-dialkyl-4-hydroxymethyl-2-methyl-1,3-dioxolane as a Raw Material The reaction which was performed in the Production Examples is as follows.

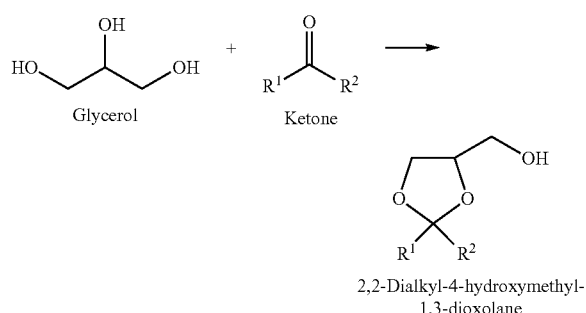

2,2-Dialkyl-4-hydroxymethyl-1,3-dioxolane

Production Example 1: Production of 2-ethyl-4-hydroxymethyl-2-methyl-1,3-dioxolane ($R^1$=Me, $R^2$=Et) as a Raw Material In a one-liter flask equipped with a Dean-Stark apparatus, 184 g of glycerol (purity: 100%, 2.00 mol), 162 g of 2-butanone (purity: 98.0%, 2.20 mol), 981 mg of methanesulfonic acid (purity: 98.0%, 10.0 mol), and 50 g of n-hexane were charged and refluxed for 5 hours while removing water by-produced by the reaction outside the reaction system. After cooling, the resultant was neutralized with 3.50 g of a 20% ethanol solution of sodium ethoxide (700 mg, 10.3 mmol as sodium ethoxide). As a result of GC analysis of the reaction solution, a reaction yield of a cis- and trans-isomer mixture of 2-ethyl-4-hydroxymethyl-2-methyl-1,3-dioxolane was 74%.

Subsequently, the reaction solution was transferred into a 500-mL flask equipped with a Claisen head; after heating at 50° C., the pressure was gradually reduced to distill off the n-hexane and ethanol; and simple distillation was further performed under reduced pressure of 0.13 kPa (absolute pressure), thereby obtaining 220 g of a stereoisomer mixture which was distilled out as a colorless liquid at a fraction temperature of 91 to 94° C. The purity was 95.3%, and the distillation yield was 97%.

<Spectral Data of Stereoisomer Mixture>
IR (neat, cm$^{-1}$): 3465 (br), 2973, 2935, 2883, 1466, 1375, 1190, 1078, 1041, 876
MS (m/z): 131, 117, 57, 43

Production Example 2: Production of 2-hydroxymethyl-1,4-dioxaspiro[4.5]decane ($R^1$ and $R^2$=—(CH$_2$)$_5$—) as a Raw Material Using 218 g of cyclohexanone (purity: 99.0%, 2.20 mol) as a reaction raw material, the same operations as in Production Example 1 were followed, thereby obtaining 2-hydroxymethyl-1,4-dioxaspiro[4.5]decane in a reaction yield of 80%.

Simple distillation was further performed under reduced pressure of 0.13 kPa (absolute pressure), thereby obtaining 297 g of a colorless liquid which was distilled out at a fraction temperature of 123 to 126° C. The purity was 97.0%, and the distillation yield was 95%.

<Spectral Data>
$^1$H-NMR (400 MHz, CDCl$_3$, $\delta_{ppm}$): 1.37-1.42 (2H, m), 1.54-1.63 (8H, m), 2.30 (1H, s), 3.56-3.61 (1H, m), 3.70-3.80 (2H, m), 4.02-4.05 (1H, m), 4.21-4.25 (1H, m)
$^{13}$C-NMR (100 MHz, CDCl$_3$, $\delta_{ppm}$): 23.7, 24.0, 25.1, 34.7, 36.3, 63.1, 65.3, 75.7, 110.0

IR (neat, cm$^{-1}$): 3423 (br), 2933, 2860, 1448, 1365, 1281, 1163, 1097, 1039, 926
MS (m/z): 172 (Mt), 143, 129, 116, 81, 73, 55, 41, 31

Example 1 and Comparative Example 1: Production of (1,3-dioxolan-4-yl)methyl 1,3-dioxolane-4-carboxylate The reaction which was performed in Example 1 and Comparative Example 1 is as follows.

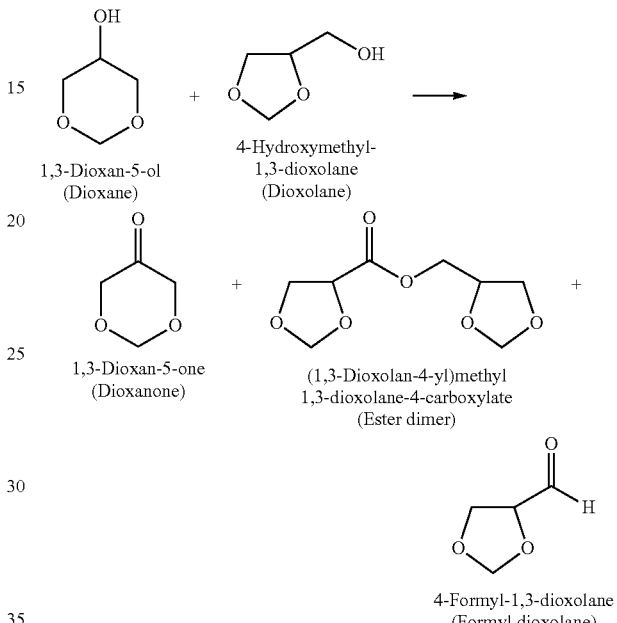

Example 1-1

In a 50-mL flask equipped with a 20-mL dropping funnel, 3.19 g of a mixture of 1,3-dioxan-5-ol and 4-hydroxymethyl-1,3-dioxolane (a trade name: Glycerol Formal, manufactured by Tokyo Chemical Industry Co., Ltd., purity: 98.0%, 30.0 mmol; Reference Literature 1 (Journal of Catalysis, Vol. 245, pp. 428-435, 2007) describes $^1$H-NMR signal assignment of a proton at the 2-position of two kinds of isomers, and an isomer ratio of 1,3-dioxan-5-ol to 4-hydroxymethyl-1,3-dioxolane determined from this information and the $^1$H-NMR analysis was 58/42), 4.7 mg of 2-hydroxy-2-azaadamantane (AZADOL, a trademark, manufactured by Nissan Chemical Corporation, purity: 98.0%, 30 μmol), 4.92 g of 3,5-lutidine (purity: 98.0%, 45.0 mmol), and 10 g of 2-butanone were charged and stirred in a nitrogen atmosphere while cooling. A solution of 2.94 g of TCCA (purity: 95.0%, 12.0 mmol) dissolved in 10 g of 2-butanone was charged in the dropping funnel and dropped over 1 hour while regulating a dropping rate such that the reaction solution temperature within the flask fell within a range of from −10° C. to 10° C. The cooling was stopped, and the stirring was further continued for 2 hours while raising the reaction solution temperature to around 25° C. Finally, 0.20 g of 2-propanol (purity: 99.7%, 3.3 mmol) was added, and the stirring was further performed for 10 minutes, thereby completing the reaction. After filtering off a by-produced powdered solid, the filtrate was subjected to GC analysis. As a result, the conversion of 4-hydroxymethyl-1,3-dioxolane was 100%, the yield of (1,3-dioxolan- 4-yl)methyl 1,3-dioxolane-4-carboxylate was 91%, and the recovery of the unreacted 3,5-lutidine relative to the charged amount was 18%.

In a stirred mixed liquid of 50 g of tert-butyl methyl ether having the whole amount of the filtration residue dispersed therein and 25 g of ion exchanged water, a 2 mol/L sodium hydroxide aqueous solution was dropped until the pH of the water layer became 12 or more. At the time of completion of dropping, the filtration residue was dissolved in oily water. As a result of GC analysis of the tert-butyl methyl ether solution from which the water layer had been removed through oil-water separation, the recovery of the 3,5-lutidine relative to the charged amount was 76%, and a total recovery was 94%.

Example 1-2

The same operations as in Example 1-1 were performed, except for changing the kinds of the base and the solvent. The reaction conditions and results of Example 1-2 are shown in the table.

Comparative Example 1-1

In a one-liter flask equipped with a 100-mL dropping funnel, 63.7 g of glycerol formal (purity: 98.0%, 600 mmol), 93.8 mg of AZADOL (purity: 98.0%, 0.60 mmol), 71.5 g of pyridine (purity: 99.5%, 900 mmol), and 150 g of acetonitrile were charged and stirred in a nitrogen atmosphere while cooling. A solution of 58.7 g of trichloroisocyanuric acid (TCCA, purity: 95.0%, 240 mmol) dissolved in 150 g of acetonitrile was charged 3 separate times in the dropping funnel and dropped over 3.5 hours while regulating a dropping rate such that the reaction solution temperature within the flask fell within a range of from −2° C. to 2° C. The cooling was stopped, and the stirring was further continued for 4 hours while raising the reaction solution temperature to around 20° C. Finally, 7.23 g of 2-propanol (purity: 99.7%, 120 mmol) was added, and the stirring was further performed for 20 minutes, thereby completing the reaction. After filtering off a by-produced powdered solid, 100 g of tert-butyl methyl ether was added to the reaction solution from which the acetonitrile had been distilled off, and the filtration-off of the deposited powdered solid and the distillation-off of the solvent were repeated two times, thereby obtaining 70.5 g of an orange-colored oily crude product. As a result of GC analysis of the crude product, the conversion of 4-hydroxymethyl-1,3-dioxolane was 100%, the yield of (1,3-dioxolan-4-yl)methyl 1,3-dioxolane-4-caboxylate was 95%, and the recovery of the unreacted pyridine relative to the charged amount was 24%.

In a stirred mixed liquid of 500 g of tert-butyl methyl ether having the whole amount of the filtration residue dispersed therein and 250 g of ion exchanged water, an 8 mol/L sodium hydroxide aqueous solution was dropped until the pH of the water layer became 12 or more. At the time of completion of dropping, the entire filtration residue was dissolved in oily water. As a result of GC analysis of the tert-butyl methyl ether solution from which the water layer had been removed through oil-water separation, the recovery of the 3,5-lutidine relative to the charged amount was 41%, and a total recovery was 65%.

In a 200-mL pear-shaped flask equipped with a packed distillation tower having the number of theoretical stages of 6 (packing: Helipack packing No. 2), 65.0 g of the crude product was charged, and 21.9 g of (1,3-dioxolan-4-yl)methyl 1,3-dioxolane-4-carboxylate which was distilled out as a pale yellow liquid at a fraction temperature of 89 to 91° C. under conditions at 0.13 kPa (absolute pressure) and at a reflux ratio of 0.1 was obtained. The purity was 98.8%, and the distillation yield was 96%. $^{13}$C-NMR analysis suggested that this ester dimer was a stereoisomer mixture of two pairs of racemates. With respect to other two pairs of racemates, it is estimated that the peaks were overlapped, so that the detection could not be performed.

Spectral Data of (1,3-Dioxolan-4-yl)methyl 1,3-Dioxolane-4-caboxylate (Stereoisomer Mixture)

IR (neat, cm$^{-1}$): 2956, 2856, 1751, 1284, 1151, 1082, 1016, 916
MS (m/z): 204 (M$^+$), 159, 129, 86, 73, 57, 45
FIG. 1 is a GC chart of the reaction solution.

Comparative Examples 1-2 and 1-3

The same operations as in Example 1-1 were performed, except for changing the kinds of the base and the solvent. The reaction conditions and results of Comparative Examples 1-2 and 1-3 are shown in the table.

Examples 2, 3, and 4 and Comparative Examples 2, 3, and 4: Production of (2,2-dialkyl-1,3-dioxolan-4-yl)methyl 2,2-dialkyl-1,3-dioxolane-4-carboxylate The reaction which was performed in the Examples is as follows.

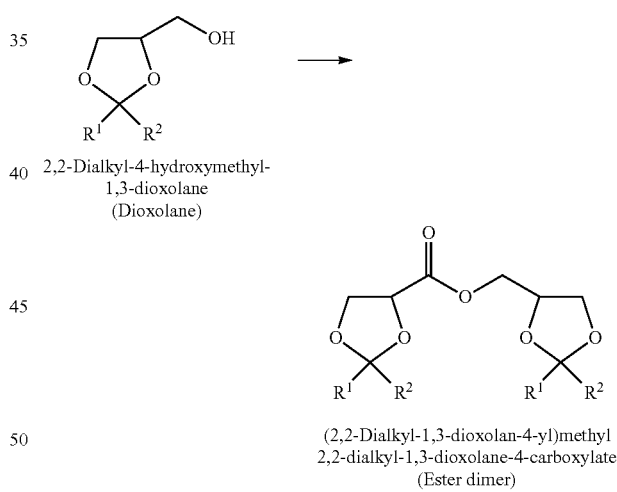

2,2-Dialkyl-4-hydroxymethyl-1,3-dioxolane
(Dioxolane)

(2,2-Dialkyl-1,3-dioxolan-4-yl)methyl
2,2-dialkyl-1,3-dioxolane-4-carboxylate
(Ester dimer)

Example 2 and Comparative Example 2: Production of (2,2-dimethyl-1,3-dioxolan-4-yl)methyl 2,2-dimethyl-1,3-dioxolane-4-carboxylate (R$^1$ and R$^2$=Me)

Example 2-1

Using, as a reaction raw material, 4.05 g of 2,2-dimethyl-4-hydroxymethyl-1,3-dioxolane (a trade name: 2,2-dimethyl-1,3-dioxolane-4-metanol, manufactured by Tokyo Chemical Industry Co., Ltd., purity: 98.0%, 30.0 mmol), the same operations as in Example 1-1 were performed, except for changing the reaction conditions as shown in the table.

As a result of GC analysis of the filtrate, the conversion of 2,2-dimethyl-4-hydroxymethyl-1,3-dioxolane was 100%, and the yield of (2,2-dimethyl-1,3-dioxolan-4-yl)methyl 2,2-dimethyl-1,3-dioxolane-4-carboxylate was 69%.

The recovery of the unreacted 2,6-lutidine in the filtrate relative to the charged amount was 15%, the recovery of the regenerated 2,6-lutdine by an alkali treatment of the filtration residue was 76%, and a total recovery was 91%.

Comparative Example 2-1

In a 300-mL flask equipped with a 100-mL dropping funnel, 20.2 g of 2,2-dimethyl-4-hydroxymethyl-1,3-dioxolane (purity: 98.0%, 150 mmol), 23.4 mg of 2-hydroxy-2-azaadamantane (AZADOL, a trademark, manufactured by Nissan Chemical Corporation, purity: 98.0%, 150 µmol), 17.9 g of pyridine (purity: 99.5%, 225 mmol), and 50 g of acetonitrile were charged and stirred in a nitrogen atmosphere while cooling. A solution of 14.7 g of trichloroisocyanuric acid (TCCA, purity: 95.0%, 60.0 mmol) dissolved in 50 g of acetonitrile was charged in the dropping funnel and dropped over 2 hours while regulating a dropping rate such that the reaction solution temperature within the flask fell within a range of from −2° C. to 10° C. The cooling was stopped, and the stirring was further continued for 3 hours while raising the reaction solution temperature to around 20° C. Finally, 1.81 g of 2-propanol (purity: 99.7%, 30.0 mmol) was added, and the stirring was further performed for 20 minutes, thereby completing the reaction. After filtering off a by-produced powdered solid, the filtrate was subjected to GC analysis. As a result, the yield of (2,2-dimethyl-1,3-dioxolan-4-yl)methyl 2,2-dimethyl-1,3-dioxolane-4-carboxylate was 70%, and the recovery of the unreacted pyridine relative to the charged amount was 19%.

In a stirred mixed liquid of 300 g of tert-butyl methyl ether having the whole amount of the filtration residue dispersed therein and 150 g of ion exchanged water, an 8 mol/L sodium hydroxide aqueous solution was dropped until the pH of the water layer became 12 or more. At the time of completion of dropping, the entire filtration residue was dissolved in oily water. As a result of GC analysis of the tert-butyl methyl ether solution from which the water layer had been removed through oil-water separation, the recovery of the pyridine relative to the charged amount was 38%, and a total recovery was 57%.

In order to remove the powdered solid deposited after distilling off the acetonitrile from the filtrate, 100 g of tert-butyl methyl ether and 50 g of ion exchanged water were added to perform extraction. After settled separation, the lower-layer water was taken out, and 50 g of ion exchanged water was again added, thereby repeating the operation of from extraction to taking-out of the lower-layer water. The resulting organic layer was dried over 20 g of anhydrous sodium sulfate, and after filtration, the tert-butyl methyl ether was distilled out, thereby obtaining 15.1 g of a dark orange-colored oily crude product. As a result of GC analysis of the crude product, the yield of (2,2-dimethyl-1,3-dioxolan-4-yl)methyl 2,2-dimethyl-1,3-dioxolane-4-carboxylate was 59%.

Subsequently, 14.1 g of the crude product was transferred into a 50-mL flask equipped with a Claisen head, and simple distillation was performed under reduced pressure of 0.13 kPa (absolute pressure), thereby obtaining 8.20 g of (2,2-dimethyl-1,3-dioxolan-4-yl)methyl 2,2-dimethyl-1,3-dioxolane-4-carboxylate which was distilled out as a colorless liquid at a fraction temperature of 103 to 106° C. The purity was 98.7%, and the distillation yield was 97%. According to the $^{13}$C-NMR analysis, this ester dimer was confirmed to be a stereoisomer mixture of two pairs of racemates.

<Spectral Data of Stereoisomer Mixture>

IR (neat, cm$^{-1}$): 2987, 2939, 1759, 1734, 1371, 1192, 1153, 1099, 1066, 837

MS (m/z): 259, 245, 186, 130, 115, 101, 73, 59, 43

Comparative Example 2-2

The same operations as in Example 2 were performed, except for changing the kind of the base. The reaction conditions and results of Comparative Example 2-2 are shown in the table.

Example 3 and Comparative Example 3: Production of (2-ethyl-2-methyl-1,3-dioxolan-4-yl)methyl 2-ethyl-2-methyl-1,3-dioxolane-4-carboxylate ($R^1$=Me, $R^2$=Et)

Example 3

Using, as a reaction raw material, 4.60 g of 2-ethyl-4-hydroxymethyl-2-methyl-1,3-dioxolane (purity: 95.3%, 30.0 mmol) obtained in Production Example 1, the same operations as in Example 1-1 were performed. As a result of GC analysis of the filtrate, the conversion of 2-ethyl-4-hydroxymethyl-2-methyl-1,3-dioxolane was 100%, and the yield of (2-ethyl-2-methyl-1,3-dioxolan-4-yl)methyl 2-ethyl-2-methyl-1,3-dioxolane-4-carboxylate was 73%.

The recovery of the unreacted 3,5-lutidine in the filtrate relative to the charged amount was 15%, the recovery of the regenerated 3,5-lutdine by an alkali treatment of the filtration residue was 66%, and a total recovery was 81%.

Comparative Example 3-1

Using, as a reaction raw material, 23.0 g of 2-ethyl-4-hydroxymethyl-2-methyl-1,3-dioxolane (purity: 95.3%, 150 mmol) obtained in Production Example 1, the same operations as in Comparative Example 2-1 were performed. As a result of GC analysis of the filtrate, the conversion of 2-ethyl-4-hydroxymethyl-2-methyl-1,3-dioxolane was 100%, and the yield of (2-ethyl-2-methyl-1,3-dioxolan-4-yl) methyl 2-ethyl-2-methyl-1,3-dioxolane-4-carboxylate was 74%.

The recovery of the unreacted pyridine in the filtrate relative to the charged amount was 21%, the recovery of the regenerated pyridine by an alkali treatment of the filtration residue was 29%, and a total recovery was 50%.

The yield of (2-ethyl-2-methyl-1,3-dioxolan-4-yl)methyl 2-ethyl-2-methyl-1,3-dioxolane-4-carboxylate as determined by GC analysis of 19.8 g of a red oily crude product obtained after a water-washing treatment of the filtrate was 72%.

Subsequently, 17.0 g of the crude product was subjected to simple distillation under reduced pressure of 40 Pa (absolute pressure), thereby obtaining 11.6 g of (2-ethyl-2-methyl-1,3-dioxolan-4-yl)methyl 2-ethyl-2-methyl-1,3-dioxolane-4-carboxylate which was distilled out as a pale yellow liquid at a fraction temperature of 119 to 122° C. The purity was 98.1%, and the distillation yield was 80%. According to the GC-MS analysis, it was suggested that this ester dimer was a stereoisomer mixture of at least three pairs of racemates. With respect to other racemates, it is estimated that the peaks were overlapped, so that the detection could not be performed.

<Spectral Data of Stereoisomer Mixture>

IR (neat, cm$^{-1}$): 2979, 2939, 2883, 1761, 1736, 1377, 1186, 1072, 874

MS (m/z, common to three peaks on GC): 287, 273, 259, 115, 57, 43

Comparative Example 3-2

The same operations as in Example 3 were performed, except for changing the kind of the base. The reaction conditions and results of Comparative Example 3-2 are shown in the table.

Example 4 and Comparative Example 4: Production of (1,4-dioxaspiro[4,5]decan-2-yl)methyl 1,4-dioxaspiro[4.5]decane-2-carboxylate ($R^1$ and $R^2$=—$(CH_2)_5$—)

Example 4

Using, as a reaction raw material, 5.32 g of 2-hydroxymethyl-1,4-dioxaspiro[4.5]decane (purity: 97.0%, 30.0 mmol) obtained in Production Example 2, the same operations as in Example 1-1 were performed. As a result of GC analysis of the filtrate, the conversion of 2-hydroxymethyl-1,4-dioxaspiro[4.5]decane was 100%, and the yield of (1,4-dioxaspiro[4.5]decan-2-yl)methyl 1,4-dioxaspiro[4.5]decane-2-carboxylate was 70%.

The recovery of the unreacted 3,5-lutidine in the filtrate relative to the charged amount was 32%, the recovery of the regenerated 3,5-lutdine by an alkali treatment of the filtration residue was 55%, and a total recovery was 87%.

Comparative Example 4-1

Using, as a reaction raw material, 26.6 g of 2-hydroxymethyl-1,4-dioxaspiro[4.5] decane (purity: 97.0%, 150 mmol) obtained in Production Example 2, the same operations as in Comparative Example 2-1 were performed. As a result of GC analysis of the filtrate, the conversion of 2-hydroxymethyl-1,4-dioxaspiro[4.5]decane was 100%, and the yield of (1,4-dioxaspiro[4.5]decan-2-yl)methyl 1,4-dioxaspiro[4.5]decane-2-carboxylate was 66%.

The recovery of the unreacted pyridine relative to the charged amount was 18%, the recovery of the regenerated pyridine by an alkali treatment of the filtration residue was 34%, and a total recovery was 52%.

The yield of (1,4-dioxaspiro[4.5]decan-2-yl)methyl 1,4-dioxaspiro[4.5]decane-2-carboxylate as determined by GC analysis of 23.5 g of a dark orange-colored oily crude product obtained after a water-washing treatment of the filtrate was 66%.

Subsequently, 6.50 g of the crude product was distilled under reduced pressure of 40 Pa (absolute pressure) with a Kugelrohr distillation apparatus, thereby obtaining 2.89 g of (1,4-dioxaspiro[4.5]decan-2-yl)methyl 1,4-dioxaspiro[4.5]decane-2-carboxylate which was distilled out as an orange-colored liquid at an apparatus temperature of 225 to 240° C. The purity was 95.6%, and the distillation yield was 60%. According to $^{13}$C-NMR analysis, this ester dimer was found to be a stereoisomer mixture of four kinds composed of two pairs of racemates.

<Spectral Data of Stereoisomer Mixture>

IR (neat, cm$^{-1}$): 2933, 2862, 1761, 1738, 1448, 1367, 1161, 1097, 922

MS (m/z): 340 (M$^+$), 311, 297, 242, 199, 141, 127, 55

Comparative Example 4-2

The same operations as in Example 4 were performed, except for changing the kind of the base. The reaction conditions and results of Comparative Example 4-2 are shown in the table.

The reaction conditions and results of the aforementioned Examples and Comparative Examples are shown in the following table.

TABLE 1-1

| | Compound A $R^1$, $R^2$ | Compound B Name | Molar ratio [1] | Oxidizing agent Name | Molar ratio [1] | Pyridine having alkyl group Name | Molar ratio [1] |
|---|---|---|---|---|---|---|---|
| Example 1-1 | H, H | AZADOL | 0.001 | TCCA | 0.40 | 3,5-Lutidine | 1.5 |
| Example 1-2 | H, H | AZADOL | 0.001 | TCCA | 0.40 | 3-Ethylpyridine | 1.5 |
| Comparative Example 1-1 | H, H | AZADOL | 0.001 | TCCA | 0.40 | Pyridine | 1.5 |
| Comparative Example 1-2 | H, H | AZADOL | 0.001 | TCCA | 0.40 | Pyridine | 1.5 |
| Comparative Example 1-3 | H, H | AZADOL | 0.001 | TCCA | 0.40 | Pyridine | 1.5 |
| Example 2-1 | Me, Me | AZADOL | 0.010 | TCCA | 0.40 | 2,6-Lutidine | 1.5 |
| Comparative Example 2-1 | Me, Me | AZADOL | 0.001 | TCCA | 0.40 | Pyridine | 1.5 |
| Comparative Example 2-2 | Me, Me | AZADOL | 0.010 | TCCA | 0.40 | Pyridine | 1.5 |

| | Solvent | Reaction time (hr) [2] | Conversion of dioxolane (%) | Yield of ester dimer (%) [3] | Recovery of pyridine (%) In filtrate | Recovery of pyridine (%) Derived from filtration residue | Total |
|---|---|---|---|---|---|---|---|
| Example 1-1 | 2-Butanone | 3 | 100 | 91 | 18 | 76 | 94 |
| Example 1-2 | Acetonitrile | 3 | 100 | 93 | 20 | 70 | 90 |
| Comparative Example 1-1 | Acetonitrile | 8 | 100 | 95 | 24 | 41 | 65 |

TABLE 1-1-continued

| | | | | | | |
|---|---|---|---|---|---|---|
| Comparative Example 1-2 | 2-Butanone | 3 | 100 | 96 | 29 | 22 | 51 |
| Comparative Example 1-3 | Acetonitrile | 3 | 100 | 96 | 20 | 37 | 57 |
| Example 2-1 | Acetonitrile | 2 | 100 | 69 | 15 | 76 | 91 |
| Comparative Example 2-1 | Acetonitrile | 5 | 100 | 70 | 19 | 38 | 57 |
| Comparative Example 2-2 | Acetonitrile | 2 | 100 | 71 | 22 | 37 | 59 |

[1]) Molar ratio relative to Compound A (dioxolane)
[2]) Time from start of dropping to completion of reaction
[3]) Results of GC analysis of filtrate after filtering off a salt of pyridine, etc.

TABLE 1-2

| | Compound A $R^1$, $R^2$ | Compound B Name | Compound B Molar ratio[1] | Oxidizing agent Name | Oxidizing agent Molar ratio[1] | Pyridine having alkyl group Name | Pyridine having alkyl group Molar ratio[1] |
|---|---|---|---|---|---|---|---|
| Example 3 | Me, Et | AZADOL | 0.010 | TCCA | 0.40 | 3,5-Lutidine | 1.5 |
| Comparative Example 3-1 | Me, Et | AZADOL | 0.001 | TCCA | 0.40 | Pyridine | 1.5 |
| Comparative Example 3-2 | Me, Et | AZADOL | 0.010 | TCCA | 0.40 | Pyridine | 1.5 |
| Example 4 | —(CH$_2$)$_5$— | AZADOL | 0.001 | TCCA | 0.40 | 3,5-Lutidine | 2.0 |
| Comparative Example 4-1 | —(CH$_2$)$_5$— | AZADOL | 0.001 | TCCA | 0.40 | Pyridine | 1.5 |
| Comparative Example 4-2 | —(CH$_2$)$_5$— | AZADOL | 0.001 | TCCA | 0.40 | Pyridine | 2.0 |

| | Solvent | Reaction time (hr)[2] | Conversion of dioxolane (%) | Yield of ester dimer (%)[3] | Recovery of pyridine (%) In filtrate | Recovery of pyridine (%) Derived from filtration residue | Recovery of pyridine (%) Total |
|---|---|---|---|---|---|---|---|
| Example 3 | Acetonitrile | 2 | 100 | 73 | 15 | 66 | 81 |
| Comparative Example 3-1 | Acetonitrile | 5 | 100 | 74 | 21 | 29 | 50 |
| Comparative Example 3-2 | Acetonitrile | 2 | 100 | 77 | 17 | 38 | 55 |
| Example 4 | Acetonitrile | 4 | 100 | 70 | 32 | 55 | 87 |
| Comparative Example 4-1 | Acetonitrile | 5 | 100 | 66 | 18 | 34 | 52 |
| Comparative Example 4-2 | Acetonitrile | 4 | 100 | 65 | 40 | 26 | 66 |

[1]) Molar ratio relative to Compound A (dioxolane)
[2]) Time from start of dropping to completion of reaction
[3]) Results of GC analysis of filtrate after filtering off a salt of pyridine, etc.

The same operations as in Examples 1 and 2 were performed, except that in Examples 1 and 2, the respective conditions of Compound A, Compound B (catalyst), oxidizing agent, base, solvent, etc. as used were changed as shown in the following Table 2. The results are shown in the following Table 2.

TABLE 2

| Example | Compound A $R^1$, $R^2$ | Compound B Name | Compound B Molar ratio[1] | Oxidizing agent Name | Oxidizing agent Molar ratio[1] | Pyridine having alkyl substituent Name | Pyridine having alkyl substituent Molar ratio[1] | Solvent | Reaction time (hr)[2] | Conversion of dioxolane (%) | Yield of ester dimer (%)[3] |
|---|---|---|---|---|---|---|---|---|---|---|---|
| 1-3 | H, H | AZADOL | 0.001 | TCCA | 0.40 | 3,5-Lutidine | 1.5 | Acetonitrile | 2 | 100 | 94 |
| 1-4 | H, H | AZADOL | 0.001 | TCCA | 0.40 | 2,6-Lutidine | 1.5 | Acetonitrile | 7 | Not analyzed | 78 |
| 1-5 | H, H | AZADOL | 0.001 | TCCA | 0.40 | 5-Ethyl-2-methyl pyridine | 2.0 | Acetonitrile | 4 | 100 | 69 |

TABLE 2-continued

| Example | ComPound A R¹, R² | Compound B Name | Molar ratio¹⁾ | Oxidizing agent Name | Molar ratio¹⁾ | Pyridine having alkyl substituent Name | Molar ratio¹⁾ | Solvent | Reaction time (hr) ²⁾ | Conversion of dioxane (%) | Yield of ester dimer (%) ³⁾ |
|---|---|---|---|---|---|---|---|---|---|---|---|
| 1-6 | H, H | 4-OMe-TEMPO | 0.010 | TCCA | 0.40 | 3,5-Lutidine | 1.5 | Acetonitrile | 3 | 100 | 100 |
| 1-7 | H, H | 4-NHAc-TEMPO | 0.003 | TCCA | 0.40 | 4-Methyl pyridine | 1.5 | Acetonitrile | 4 | 100 | 93 |
| 1-8 | H, H | 4-NHAc-TEMPO | 0.003 | TCCA | 0.40 | 4-Ethyl pyridine | 1.5 | Acetonitrile | 4 | 100 | 72 |
| 1-9 | H, H | 4-OMe-TEMPO | 0.003 | TCCA | 0.40 | 5-Ethyl-2-methyl pyridine | 1.5 | 2-Butanone | 4 | 99 | 43 |
| 1-10 | H, H | 4-NHAc-TEMPO | 0.010 | TCCA | 0.40 | 2,6-Di-tert-butylpyridine | 1.5 | Acetonitrile | 3 | 100 | 37 |
| 1-11 | H, H | 4-NHAc-TEMPO salt ⁴⁾ | 0.003 | TCCA | 0.40 | 4-Methyl pyridine | 1.5 | 2-Butanone | 4 | 100 | 83 |
| 1-12 | H, H | 4-NHAc-TEMPO salt ⁴⁾ | 0.003 | TCCA | 0.40 | 2,6-Lutidine | 1.5 | 2-Butanone | 4 | 99 | 44 |
| 2-2 | Me, Me | 4-NHAc-TEMPO | 0.010 | TCCA | 0.40 | 3,5-Lutidine | 1.5 | Acetonitrile | 3 | 100 | 55 |
| 2-3 | Me, Me | 4-NHAc-TEMPO | 0.010 | TCCA | 0.40 | 2,6-Lutidine | 1.5 | Acetonitrile | 3 | 97 | 42 |
| 2-4 | Me, Me | 4-NHAc-TEMPO salt ⁴⁾ | 0.010 | TCCA | 0.40 | 3,5-Lutidine | 1.5 | Acetonitrile | 2 | 100 | 42 |
| 2-5 | Me, Me | 4-NHAc-TEMPO salt ⁴⁾ | 0.010 | TCCA | 0.40 | 4-Methyl pyridine | 1.5 | Acetonitrile | 2 | 92 | 37 |
| Comp. Example 2-3 | Me, Me | 4-NHAc-TEMPO salt ⁴⁾ | 2.4 | None | | 2,6-Lutidine | 2.2 | Acetonitrile | 2 | 90 | 1 |

¹⁾Molar ratio relative to Compound A (dioxolane)
²⁾Time from start of dropping to completion of reaction
³⁾Results of GC analysis of filtrate after filtering off a salt of pyridine, etc.
⁴⁾4-Acetamido-2,2,6,6-tetramethyl-1-oxopiperidinum tetrafluoroborate

Example 5: Production of Ethyl Glycerate

The reaction which was performed in Example 5 is as follows.

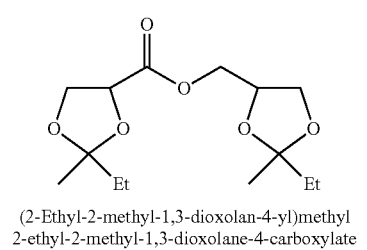

(2-Ethyl-2-methyl-1,3-dioxolan-4-yl)methyl 2-ethyl-2-methyl-1,3-dioxolane-4-carboxylate

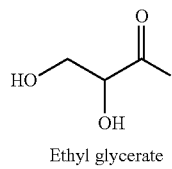

Ethyl glycerate

In a 100-mL flask, 5.00 g of (2-ethyl-2-methyl-1,3-dioxolan-4-yl)methyl 2-ethyl-2-methyl-1,3-dioxolane-4-carboxylate (purity: 98.1%, 17.0 mmol) obtained in Comparative Example 3, 83 mg of methanesulfonic acid (purity: 98.0%, 0.85 mmol), and 39.4 g of ethanol (purity: 99.5%, 850 mmol) were charged and refluxed for 2 hours. After cooling, the resultant was neutralized with 290 mg of a 20% ethanol solution of sodium ethoxide (58 mg, 0.85 mmol as sodium ethoxide), and the ethanol was distilled off. Subsequently, 8.75 g of the resulting orange-colored oily crude product was purified with a Kugelrohr distillation apparatus. There was thus obtained 1.53 g of ethyl glycerate which was distilled out as a colorless liquid under conditions at 0.13 kPa (absolute pressure) and at an apparatus temperature of 150 to 155° C. The purity was 93.5%, and the yield was 63%.

<Spectral Data of Ethyl Glycerate>
¹H-NMR (400 MHz, CDCl₃, $\delta_{ppm}$): 1.31 (3H, t, J=6.8 Hz), 3.82-3.92 (2H, m), 4.24-4.30 (3H, m); the ¹H peak of the hydroxy group became broad, so that it could not be detected.
¹³C-NMR (100 MHz, CDCl₃, $\delta_{ppm}$): 14.1, 62.0, 64.1, 71.8, 173.0
IR (neat, cm⁻¹): 3425 (br), 2974, 2935, 1728, 1201, 1111, 1063, 1020
MS (m/z): 134 (M⁺), 104, 76, 61, 43, 31

INDUSTRIAL APPLICABILITY

In accordance with the production method of the present invention, the ester dimer of the present invention (glyceric acid ester in which hydroxy groups at the 2-position and 3-position are protected as a cyclic acetal group) is obtained easily and in a high yield, and furthermore, it is easy to reuse the pyridine to be used for the reaction. The ester dimer obtained by the present invention is, for example, useful as synthetic intermediates, such as glyceric acid and a deprotected glyceric acid ester, which are used as raw materials for various medicaments, cosmetics, detergents, polymers, and so on.

The invention claimed is:

1. A method of producing a compound represented by the following formula (II), comprising a step of oxidatively esterifying Compound A, Compound A being represented by the following formula (I), with Compound B, Compound B being selected from an organic nitroxyl radical, an N-hydroxy form thereof, and a salt containing an oxo ammonium cation of them, and an oxidizing agent, and in the presence of a pyridine having an alkyl substituent, wherein the molar ratio of Compound B to Compound A (B:A) used in the oxidative esterification is in the range from 0.0001:1 through 0.1:1:

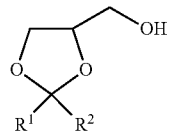
(I)

wherein, in the formula (I), $R^1$ and $R^2$ each independently represent a hydrogen atom or a monovalent hydrocarbon group, or $R^1$ and $R^2$ are bonded to each other to form a divalent hydrocarbon group for constituting a ring structure; and

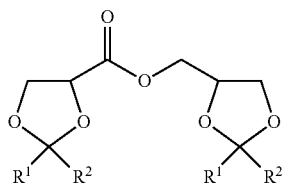
(II)

wherein, in the formula (II), $R^1$ and $R^2$ each independently represent a hydrogen atom or a monovalent hydrocarbon group, or $R^1$ and $R^2$ are bonded to each other to form a divalent hydrocarbon group for constituting a ring structure.

2. The production method according to claim 1, wherein in Compound A, $R^1$ is a hydrogen atom, and $R^2$ is a hydrogen atom or a monovalent hydrocarbon group.

3. The production method according to claim 1, wherein in Compound A, $R^1$ and $R^2$ are each a monovalent hydrocarbon group.

4. The production method according to claim 1, wherein the pyridine having an alkyl substituent is a pyridine having an alkyl substituent at at least one position selected from the 3-position, the 4-position, and the 5-position and not having an alkyl substituent at the 2-position and the 6-position; and Compound B is a compound selected from an organic nitroxyl radical and a salt containing an oxo ammonium cation thereof.

5. The production method according to claim 1, wherein Compound B is an N-hydroxy form of an organic nitroxyl radical.

6. The production method according to claim 1, wherein the alkyl substituent each independently has 1 or more and 4 or less carbon atoms.

7. The production method according to claim 1, comprising a step of oxidatively esterifying a mixture of a compound represented by the following formula (I) and a compound represented by the following formula (V):

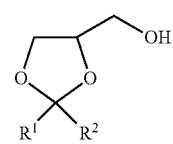
(I)

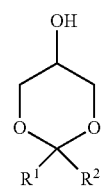
(V)

wherein, in the formulae (I) and (V), $R^1$ and $R^2$ each independently represent a hydrogen atom or a monovalent hydrocarbon group, or $R^1$ and $R^2$ are bonded to each other to form a divalent hydrocarbon group for constituting a ring structure.

8. The production method according to claim 1, wherein the organic nitroxyl radical is a compound represented by the following formula (VIII), a compound represented by the following formula (IX), or a compound represented by the following formula (X):

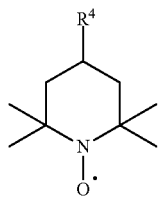
(VII)

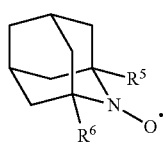
(IX)

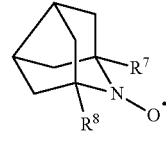
(X)

wherein, in the formula (VIII), $R^4$ represents a hydrogen atom, a halogen atom, a hydroxy group, an alkoxy group, an acyloxy group, art alkoxycarbonyl group, an amino group, an acylamino group, a sulfonyloxy group, an N-alkylcarbamoyloxy group, a carboxy group, a cyano group, an isocyanato group, an isothiocyanato group, or an oxo group; in the formula (IX), $R^5$ and $R^6$ each independently represent a hydrogen atom or a methyl group; and, in the formula (X), $R^7$ and $R^8$ each independently represent a hydrogen atom or a methyl group.

9. The production method according to claim 1, wherein the oxidizing agent is an oxidizing agent composed of a compound containing chlorine.

10. The production method according to claim 1, comprising, after the step of oxidatively esterifying the compound represented by the formula (I), a step of separating the compound represented by the formula (II).

11. The production method according to claim 10, wherein the step of separating the compound represented by the formula (II) is separation through distillation.

* * * * *